(12) United States Patent
Debnath et al.

(10) Patent No.: US 11,530,433 B2
(45) Date of Patent: Dec. 20, 2022

(54) ARTIFICIAL SECRETION PEPTIDES FOR HETEROLOGOUS PROTEIN PRODUCTION

(71) Applicant: President and Fellows of Harvard College, Cambridge, MA (US)

(72) Inventors: Anik Debnath, Cambridge, MA (US); George Church, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 339 days.

(21) Appl. No.: 16/757,687

(22) PCT Filed: Oct. 19, 2018

(86) PCT No.: PCT/US2018/056610
§ 371 (c)(1),
(2) Date: Apr. 20, 2020

(87) PCT Pub. No.: WO2019/079663
PCT Pub. Date: Apr. 25, 2019

(65) Prior Publication Data
US 2020/0270666 A1 Aug. 27, 2020

Related U.S. Application Data

(60) Provisional application No. 62/691,553, filed on Jun. 28, 2018, provisional application No. 62/676,203, filed on May 24, 2018, provisional application No. 62/584,367, filed on Nov. 10, 2017, provisional application No. 62/575,350, filed on Oct. 20, 2017.

(51) Int. Cl.
| | |
|---|---|
| *A61K 35/747* | (2015.01) |
| *A61K 35/00* | (2006.01) |
| *C12N 15/74* | (2006.01) |
| *C07K 14/47* | (2006.01) |
| *C12P 21/02* | (2006.01) |
| *C07K 14/54* | (2006.01) |
| *C07K 14/605* | (2006.01) |

(52) U.S. Cl.
CPC ............ *C12P 21/02* (2013.01); *A61K 35/747* (2013.01); *C07K 14/4723* (2013.01); *C07K 14/5428* (2013.01); *C07K 14/605* (2013.01); *C12N 15/746* (2013.01); *A61K 2035/115* (2013.01)

(58) Field of Classification Search
None
See application file for complete search history.

(56) References Cited

U.S. PATENT DOCUMENTS

| | | |
|---|---|---|
| 5,733,540 A | 3/1998 | Lee |
| 6,372,209 B1 | 4/2002 | Chrisope |
| 7,179,458 B2 | 2/2007 | Chang et al. |
| 8,853,382 B2 | 10/2014 | Hammarstrom et al. |
| 2008/0051317 A1 | 2/2008 | Church et al. |
| 2009/0226418 A1 | 9/2009 | Frenken et al. |
| 2010/0143305 A1 | 6/2010 | Lemke et al. |
| 2011/0104121 A1 | 5/2011 | Wira et al. |
| 2013/0121915 A1 | 5/2013 | Paas et al. |
| 2015/0284813 A1 | 10/2015 | Kim et al. |

FOREIGN PATENT DOCUMENTS

WO    WO 2011/160062 A2    12/2011

OTHER PUBLICATIONS

Invitation to Pay Additional Fees mailed Dec. 26, 2018, for Application No. PCT/US2018/056610.
International Search Report and Written Opinion dated Feb. 15, 2019, for Application No. PCT/US2018/056610.
International Preliminary Report on Patentability dated Apr. 30, 2020, for Application No. PCT/US2018/056610.
Deber et al., TM Finder: a prediction program for transmembrane protein segments using a combination of hydrophobicity and nonpolar phase helicity scales. Protein Sci. Jan. 2001;10(1):212-9. doi: 10.1110/ps.30301.
Kovacs et al., Determination of intrinsic hydrophilicity/hydrophobicity of amino acid side chains in peptides in the absence of nearest-neighbor or conformational effects. Biopolymers. 2006;84(3):283-97. doi: 10.1002/bip.20417. Author Manuscript.
Lebeer et al., Exopolysaccharides of Lactobacillus rhamnosus GG form a protective shield against innate immune factors in the intestine. Microb Biotechnol. May 2011;4(3):368-74. doi: 10.1111/j.1751-7915.2010.00199.x. Epub Aug. 17, 2010.
Marcobal et al., Expression of Human Immunodeficiency Virus Type 1 Neutralizing Antibody Fragments Using Human Vaginal Lactobacillus. AIDS Res Hum Retroviruses. Oct. 2016/Nov. 32(10-11):964-971. doi: 10.1089/AID.2015.0378. Epub Apr. 13, 2016.
Mata-Fink et al., Rapid conformational epitope mapping of anti-gp120 antibodies with a designed mutant panel displayed on yeast. J Mol Biol. Jan. 23, 2013;425(2):444-56. doi: 10.1016/j.jmb.2012.11.010. Epub Nov. 15, 2012. Author Manuscript.
Mathiesen et al., Genome-wide analysis of signal peptide functionality in Lactobacillus plantarum WCFS1. BMC Genomics. Sep. 10, 2009;10:425(1-13). doi: 10.1186/1471-2164-10-425.
Matz et al., Straightforward selection of broadly neutralizing single-domain antibodies targeting the conserved CD4 and coreceptor binding sites of HIV-1 gp120. J Virol. Jan. 2013;87(2):1137-49. doi: 10.1128/JVI.00461-12. Epub Nov. 14, 2012.
McCoy et al., Potent and broad neutralization of HIV-1 by a llama antibody elicited by immunization. J Exp Med. 2012;209(6):1091-1103. doi: 10.1084/jem.20112655.
Ryan et al., Recombinant Incretin-Secreting Microbe Improves Metabolic Dysfunction in High-Fat Diet Fed Rodents. Sci Rep. Oct. 19, 2017;7(1):13523. doi: 10.1038/s41598-017-14010-x. Erratum in: Sci Rep. Feb. 6, 2020;10(1):2392.
Steidler et al., Treatment of Murine Colitis by Lactococcus lactis secreting Interleukin-10. Science. Aug. 25, 2000;289(5483):1352-5.

(Continued)

*Primary Examiner* — Sarvamangala Devi
(74) *Attorney, Agent, or Firm* — Wolf, Greenfield & Sacks, P.C.

(57) ABSTRACT

Provided herein, in some embodiments, are artificial secretion peptides capable of directing secretion from *Lactobacillus* for use, for example, in producing heterologous proteins, including therapeutic proteins.

12 Claims, 14 Drawing Sheets

Specification includes a Sequence Listing.

(56) References Cited

OTHER PUBLICATIONS

Vandenbroucke et al., Orally administered L. lactis secreting an anti-TNF Nanobody demonstrate efficacy in chronic colitis. Mucosal Immunol. Jan. 2010;3(1):49-56. doi: 10.1038/mi.2009.116. Epub Sep. 30, 2009.
Wu et al., Engineering disulfide bridges to dissect antimicrobial and chemotactic activities of human beta-defensin 3. Proc Natl Acad Sci USA. Jul. 22, 2003;100(15):8880-5. doi: 10.1073/pnas.1533186100. Epub Jul. 2, 2003.
EP 18869030.9, Jul. 21, 2021, Partial Supplementary European Search Report.
EP 18869030.9, Oct. 21, 2021, Extended European Search Report.
Partial Supplementary European Search Report dated Jul. 21, 2021 for European Application No. EP 18869030.9.
Extended European Search Report dated Oct. 21, 2021 for European Application No. EP 18869030.9.
Mathiesen et al., Heterologous protein secretion by Lactobacillus plantarum using homologous signal peptides. J Appl Microbiol. Jul. 2008;105(1):215-26. Epub Feb. 20, 2008.
Steidler, In situ delivery of cytokines by genetically engineered Lactococcus lactis. Antonie Van Leeuwenhoek. Aug. 2002;82(1-4):323-31.
PCT/US2018/056610, Dec. 26, 2018, Invitation to Pay Additional Fees.
PCT/US2018/056610, Feb. 15, 2019, International Search Report and Written Opinion.
PCT/US2018/056610, Apr. 30, 2020, International Preliminary Report on Patentability.

ARTIFICIAL SECRETION PEPTIDES FOR HETEROLOGOUS PROTEIN PRODUCTION

RELATED APPLICATIONS

This application is a national stage filing under 35 U.S.C. § 371 of International Application Serial No. PCT/US2018/056610, filed Oct. 19, 2018, which claims the benefit under 35 U.S.C. § 119(e) of U.S. provisional application No. 62/575,350, filed Oct. 20, 2017, U.S. provisional application No. 62/584,367, filed Nov. 10, 2017, U.S. provisional application No. 62/676,203, filed May 24, 2018, and U.S. provisional application No. 62/691,553 filed Jun. 28, 2018, each of which is incorporated by reference herein in its entirety.

FEDERALLY SPONSORED RESEARCH

This invention was made with government support under Grant No. DE-FG02-02ER63445 awarded by Department of Energy. The government has certain rights in the invention.

BACKGROUND

Most secretory proteins have an N-terminal signal peptide that directs translocation across membranes in the secretory pathway. These peptides are usually 15-60 amino acids long and may be characterized by an N-terminal region that typically comprises positively charged amino acids, a central hydrophobic region, and a short C-terminal region. In prokaryotes, including bacteria, secretion signal peptides often direct cellular export through the Sec translocase. In nature, every protein exported via the Sec pathway is conjoined to its own unique secretion signal.

SUMMARY

Provided herein are versatile, artificial secretion signal peptides that enable efficient and robust production of a variety of different therapeutic proteins. Existing therapeutic protein production technology relies heavily on the use of a small set of naturally-occurring secretion signal peptides. The performance of these naturally-occurring peptides, however, is often unpredictable, resulting in inefficient/ineffective export and/or unfolded/misfolded proteins. Further, the performance of such secretion signal peptides is not necessarily transferrable among different proteins. For instance, a signal peptide that directs secretion of one protein often cannot promote secretion of another. Furthermore, previously characterized natural signal peptides that functionally secrete a protein in one bacterial strain often fail to promote secretion of the same protein in other closely related bacterial strains. The artificial secretion signal peptides of the present disclosure reliably promote secretion a variety of heterologous proteins (e.g., therapeutic proteins).

The present disclosure is based, at least in part, on unexpected data showing that artificial secretion signal peptides comprising an amino acid sequence identified by any one of SEQ ID NO:1, SEQ ID NO:3, SEQ ID NO: 5, SEQ ID NO: 11, or SEQ ID NO:7 are capable of directing secretion of functional heterologous proteins from *Lactobacilli*.

Thus, provided herein, in some aspects, are artificial secretion signal peptides comprising an amino acid sequence that is at least 90% identical to an amino acid sequence selected from the group consisting of SEQ ID NO:1, SEQ ID NO:3, SEQ ID NO:5, SEQ ID NO: 11, or SEQ ID NO:7.

Also provide herein are proteins (e.g., therapeutic proteins) fused to the artificial secretion signal peptides.

Further provided herein are nucleic acids encoding the artificial secretion signal peptides or proteins fused to the artificial secretion signal peptides.

Further still, the present disclosure provides vectors and cells (e.g., *Lactobacillus* cells) comprising the nucleic acids described herein.

The present disclosure also provides methods of producing proteins, compositions comprising the proteins, and methods of using the compositions and proteins.

The present disclosure further provides methods that include (a) computing an amino acid residue position weight matrix (PWM) for a population of signal sequences within a library of bacterial strain-specific sequences, and (b) generating a consensus signal peptide sequence based on the PWM for the population of signal sequences. In some embodiments, the methods further include (c) expressing in cells of the bacterial strain a heterologous protein of interest linked to a signal peptide comprising the consensus signal peptide sequence. The bacterial strain may be, for example, *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. In some embodiments, the bacterial cells are probiotic cells.

In some embodiments, the heterologous protein of interest is a therapeutic protein, such as an antibody. An antibody, for example, may be directed at (specific to) host tissue antigens (e.g., TNFα, or epithelial or mucosal surface proteins) or at foreign antigens (e.g., pathogenic bacteria, viruses, and toxin proteins).

In some embodiments, the nucleic acid encoding the heterologous protein of interest linked to the consensus signal peptide sequence is operably linked to an inducible promoter.

Other aspects of the present disclosure provide methods comprising administering to a subject having an inflammatory bowel disease an engineered *Lactobacillus rhamnosus* cell comprising a nucleic acid encoding an anti-inflammatory cytokine fused to an artificial secretion signal peptide derived from *Lactobacillus rhamnosus*. In some embodiments, the artificial secretion signal peptide comprises an amino acid sequence that has at least 95% identity to an amino acid sequence of SEQ ID NO: 5. In some embodiments, the artificial secretion signal peptide comprises an amino acid sequence of SEQ ID NO: 5. In some embodiments, the anti-inflammatory cytokine is IL10.

In some embodiments, the amount of anti-inflammatory cytokine produced in the subject by the engineered *Lactobacillus rhamnosus* cell, optionally following a single dose of the engineered *Lactobacillus rhamnosus* cell, is at least 2 times, at least 5 times, or at least 10 times greater than the amount of anti-inflammatory cytokine produced under control conditions. In some embodiments, the control conditions include a *Lactobacillus* cell engineered to secrete the anti-inflammatory cytokine. In some embodiments, the level of colonic IL10 present in the subject, optionally following a single dose of the engineered *Lactobacillus rhamnosus* cell, is increased by at least 25%, at least 35%, or at least 45%, relative to baseline (average IL10 levels within three months prior to administration of the engineered *L. rhamnosus* cell).

BRIEF DESCRIPTION OF THE DRAWINGS

FIG. 12A includes data indicating that *L. gasseri* SP1 (SEQ ID NO: 3) is capable of secreting anti-Shiga toxin (Stx2) antibody fragments with one, two and three antigen binding sites in *L. gasseri*. Western blots were used to visualize the relative amount of each secreted antibody fragment for three replicates using the indicated bacteria. The anti-Shiga toxin monomer is a conventional, single monomer (17 kDa), and the dimer (33.5 kDa) and trimer (48 kDa) are two and three fused monomers, respectively. Each was exposed to an anti-purification staining tag for 20 minutes. Western blot results, using anti-eTag detection antibody with chemiluminescent exposure against secreted Shiga toxin (Stx2) using the engineered *L. gasseri* comprising *L. gasseri* SP1 is shown.

DETAILED DESCRIPTION

Figure 1A:
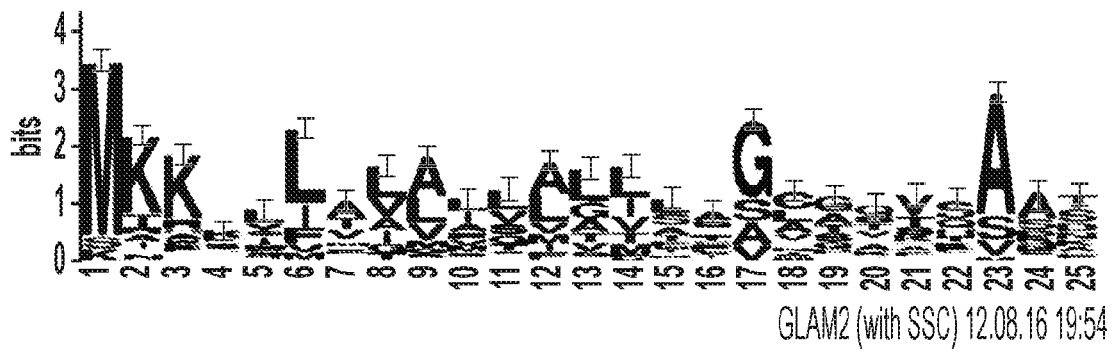
FIG. 1 includes sequence logos indicating the probability of each amino acid at each position of the secretion signal peptide for *Lactobacillus*. The sequence logos were generated by computing amino acid residue position weight matrices (PWM). Panel A: shows a sequence logo for the secretion signal peptide for *L. rhamnosus* (*L. rhamnosus* SP1). Panel B: shows a sequence logo for a secretion signal peptide sequence for *L. gasseri* (*L. gasseri* SP1). Panel C: shows a sequence logo for a secretion signal peptide sequence for *L. rhamnosus* (*L. rhamnosus* SP2)

The present disclosure, in some aspects, provides artificial secretion signal peptides for use, for example, in therapeutic protein production by *Lactobacillus* cells.

Artificial Secretion Signal Peptides

The present disclosure provides artificial secretion signal peptides that promote secretion of a variety of proteins. Artificial secretion signal peptides are secretion signal peptides that do not occur in nature. Artificial sequences may be produced recombinantly or synthetically, for example. Secretion signal peptides, generally, are short peptides (e.g., 15-60 amino acids) present at the N-terminus of newly synthesized proteins that enter the secretory pathway. Artificial secretion signal peptides of the present disclosure, in some embodiments, include an amino acid sequence that is at least 90% identical to an amino acid sequence selected from the group consisting of SEQ ID NO:1, SEQ ID NO:3, SEQ ID NO:5, SEQ ID NO: 11, and SEQ ID NO:7.

In some embodiments, the amino acid sequence is at least 95% identical to the amino acid sequence identified by SEQ ID NO:1. In some embodiments, the amino acid sequence is at least 98% identical to the amino acid sequence identified by SEQ ID NO:1. In some embodiments, the amino acid sequence is identical to the amino acid sequence identified by SEQ ID NO:1.

In some embodiments, the amino acid sequence is at least 95% identical to the amino acid sequence identified by SEQ ID NO:3. In some embodiments, wherein the amino acid sequence is at least 98% identical to the amino acid sequence identified by SEQ ID NO:3. In some embodiments, the amino acid sequence is identical to the amino acid sequence identified by SEQ ID NO:3.

In some embodiments, the amino acid sequence is at least 95% identical to the amino acid sequence identified by SEQ ID NO:5. In some embodiments, the amino acid sequence is at least 98% identical to the amino acid sequence identified by SEQ ID NO:5. In some embodiments, the amino acid sequence is identical to the amino acid sequence identified by SEQ ID NO:5.

In some embodiments, the amino acid sequence is at least 95% identical to the amino acid sequence identified by SEQ ID NO:7. In some embodiments, the amino acid sequence is at least 98% identical to the amino acid sequence identified by SEQ ID NO:7. In some embodiments, the amino acid sequence is identical to the amino acid sequence identified by SEQ ID NO:7.

In some embodiments, the amino acid sequence is at least 95% identical to the amino acid sequence identified by SEQ ID NO: 11.

Also provided herein are nucleic acids encoding the artificial secretion signal peptides. A nucleic acid is at least two nucleotides covalently linked together, and in some instances, may contain phosphodiester bonds (e.g., a phosphodiester "backbone"). The nucleic acids described herein may be generated using recombinant or synthetic technology. In some embodiment, a nucleic acid encoding an artificial signal peptide is at least 90% identical to the nucleic acid sequence identified by any one of SEQ ID NO:2, SEQ ID NO:4, or SEQ ID NO:6.

In some embodiments, the nucleic acid is at least 95% identical to the nucleic acid sequence of SEQ ID NO:2. In some embodiments, the nucleic acid is at least 98% identical to the nucleic acid sequence of SEQ ID NO:2. In some embodiments, the nucleic acid is identical to the nucleic acid sequence of SEQ ID NO:2.

In some embodiments, the nucleic acid is at least 95% identical to the nucleic acid sequence of SEQ ID NO:4. In some embodiments, the nucleic acid is at least 98% identical to the nucleic acid sequence of SEQ ID NO:4. In some embodiments, the nucleic acid is identical to the nucleic acid sequence of SEQ ID NO:4.

In some embodiments, the nucleic acid is at least 95% identical to the nucleic acid sequence of SEQ ID NO:6. In some embodiments, the nucleic acid is at least 98% identical to the nucleic acid sequence of SEQ ID NO:6. In some embodiments, the nucleic acid is identical to the nucleic acid sequence of SEQ ID NO:6.

In some embodiments, the nucleic acid is at least 95% identical to the nucleic acid sequence of SEQ ID NO:8. In some embodiments, the nucleic acid is at least 98% identical to the nucleic acid sequence of SEQ ID NO:8. In some embodiments, the nucleic acid is identical to the nucleic acid sequence of SEQ ID NO:8.

In some embodiments, the nucleic acid is codon-optimized. In some embodiments, the nucleic acid is not codon-optimized.

It should be understood that the present disclosure encompasses the use of any one or more of the artificial secretion signal peptides described herein as well as artificial secretion signal peptides that share a certain degree of sequence identity with a reference artificial signal peptide (e.g., SEQ ID NO:1, SEQ ID NO:3, SEQ ID NO:5, SEQ ID NO: 11, or SEQ ID NO:7). Percent identity refers to a relationship between the sequences of two or more polypeptides (e.g., proteins and peptides) or polynucleotides (nucleic acids), as determined by comparing the sequences. Identity measures the percent of identical matches between the smaller of two or more sequences with gap alignments (if any) addressed by a particular mathematical model or computer program (e.g., "algorithms"). Identity of related molecules can be readily calculated by known methods. "Percent (%) identity" as it applies to amino acid or nucleic acid sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Identity depends on a calculation of percent identity but may differ in value due to gaps and penalties introduced in the calculation. Variants of a particular sequence may have at least 90%, 91%, 92%, 93%, 94%, 95%, 96%, 97%, 98%, 99% but less than 100% sequence identity to that particular reference sequence identity to that particular reference sequence, as determined by sequence alignment programs and parameters described herein and known to those skilled in the art.

The comparison of sequences and determination of percent identity between two sequences can be accomplished using a mathematical algorithm. Techniques for determining identity are codified in publicly available computer programs. Exemplary computer software to determine homology between two sequences include, but are not limited to, the GCG program package (Devereux, J. et al. Nucleic Acids Research, 12(1): 387, 1984), the BLAST suite (Altschul, S. F. et al. Nucleic Acids Res. 25: 3389, 1997), and FASTA (Altschul, S. F. et al. J. Molec. Biol. 215: 403, 1990). Other techniques include: the Smith-Waterman algorithm (Smith, T. F. et al. J. Mol. Biol. 147: 195, 1981; the Needleman-Wunsch algorithm (Needleman, S. B. et al. J. Mol. Biol. 48: 443, 1970; and the Fast Optimal Global Sequence Alignment Algorithm (FOGSAA) (Chakraborty, A. et al. Sci Rep.3: 1746, 2013).

In some embodiments, an artificial secretion peptide described herein may contain a conservative amino acid substitution relative to a reference sequence disclosed herein (e.g., SEQ ID NO:1, SEQ ID NO:3, SEQ ID NO:5, SEQ ID NO: 11, or SEQ ID NO:7). A conservative amino acid substitution is an amino acid substitution that does not alter the relative charge or size characteristics of the protein or peptide in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. In some embodiments, an artificial secretion signal peptide comprises a conservative amino acid substitution relative to a reference sequence disclosed herein (e.g., SEQ ID NO:1, SEQ ID NO:3, SEQ ID NO:5, SEQ ID NO: 11, or SEQ ID NO:7), such that the hydrophobicity and/or helicity profile of a motif (e.g., hydrophilic head motif, hydrophobic core motif, or Type I Signal Peptidase cleavage site) is preserved relative to the reference sequence. For example, see Example 7 below. In some embodiments, hydrophobicity is measured by calculating $\Delta t_{R(Gly)}$. See, e.g., Kovacs et al., Biopolymers. 2006; 84(3):283-97. In some embodiments, helicity is measured by calculating $P_\alpha$. See, e.g., Deber et al., Protein Sci. 2001 January; 10(1):212-9.

Variants can be prepared according to methods for altering polypeptide sequences known to one of ordinary skill in the art such as those are found in references that compile such methods (see, e.g., Current Protocols in Molecular Biology, Ausubel, F. M., et al., New York: John Wiley & Sons, 2006; Molecular Cloning: A Laboratory Manual, Green, M. R. and Sambrook J., New York: Cold Spring Harbor Laboratory Press, 2012; Gibson, D. G., et al., Nature Methods 6(5):343-345 (2009), the teachings of which relating to polypeptide preparation and modifications are herein incorporated by reference).

Heterologous Proteins

The artificial secretion signal peptides of the present disclosure promote secretion of a heterologous protein from *Lactobacillus* cells. Thus, provided herein are nucleic acids encoding heterologous proteins fused to an artificial secretion signal peptide. Also provided herein are full-length, functional proteins encoded by the nucleic acids. A heterologous protein, with reference to a particular cell, is a protein not naturally (normally) produced by that cell. A heterologous protein, as provided herein, may be any protein not naturally produced by a *Lactobacillus* cell. In nature, unique secretion signal peptides are conjoined to each protein exported via the Sec pathway. Thus, there may be numerous different secretion signal peptides within a naturally-occurring *Lactobacillus* cell and the secretion signal peptides are often not interchangeable (e.g. cannot drive secretion of a different protein). Surprisingly, the artificial secretion sequences disclosed herein are versatile and may be used to secrete a variety of heterologous proteins (including heterologous peptides).

As a non-limiting example, a heterologous protein of the present disclosure may be 1 to 10,000 amino acids in length. In some embodiments, a heterologous protein is 1-100 amino acids in length, 1-25 amino acids in length, 1-50 amino acids in length, 10-50 amino acids in length, 50-100 amino acids in length, 100-200 amino acids in length, 200-300 amino acids in length, 300-400 amino acids in length, 400-500 amino acids in length 500-1,000 amino acids in length, 1,000-5,000 amino acids in length, or 5,000-10,000 amino acids in length. In some embodiments, a heterologous protein is 1 kDa to 10 kDa, 1 kDa to 100 kDa, 1 kDa to 1,000 kDa or 1 kDa to 5,000 kDa. In some embodiments, a heterologous protein is 2 kDa to 5 kDa in size.

The heterologous protein may be a therapeutic protein (including prophylactic proteins and/or diagnostic proteins). Non-limiting examples of therapeutic proteins include antibodies, enzymes, hormones (e.g., glucagon-like peptide 1 (GLP1)), growth factors (e.g., TGFβ), cytokines (e.g., IL10), plasma proteins, fusion proteins, membrane-lytic proteins, coagulation factors, and antimicrobial peptides. In some embodiments, a therapeutic protein is an inflammatory agent. In some embodiments, a therapeutic protein is an anti-inflammatory agent. In some embodiments, a therapeutic protein is an immunomodulatory agent. In some embodiments, a therapeutic protein is an anti-cancer agent. In some embodiments, a therapeutic protein is a metabolic agent. In some embodiments, a therapeutic protein is an antiviral/virocidal agent. In some embodiments, a therapeutic protein is an antibacterial/bacteriocidal agent (e.g., antibacterial peptide, such as defensin (e.g., human beta defensin 1

(hBD1) or beta defensin 2 (hBD2)), LL-37, dermaseptin, HCV C5alpha peptide, Magainin, or any antimicrobial peptide of bacterial origin).

The antimicrobial/bacteriocidal activity of a heterologous protein produced by any of the engineered *Lactobacillus* cells described herein, or of supernatant from an engineered *Lactobacillus* cell culture, may be measured by any method known in the art. As a non-limiting example, the ability of a heterologous protein or supernatant comprising the heterologous protein to inhibit growth of a microbe may be tested as described in Example 10. A heterologous protein produced by any of the engineered *Lactobacillus* cells described herein or supernatant from an engineered *Lactobacillus* cell culture may inhibit growth of a microbe (e.g., a pathogenic bacteria) by at least 5%, at least 10%, at least 20%, at least 30%, at least 40%, at least 50%, at least 60%, at least 70%, at least 80%, at least 90%, at least 95%, or by 100%.

In some embodiments, the therapeutic protein is an antibody. The term "antibody" encompasses whole antibodies (immunoglobulins having two heavy chains and two light chains), and antibody fragments. Antibody fragments include, but are not limited to, camelid antibodies, heavy chain fragments (VHH), Fab fragments, F(ab')$_2$ fragments, nanobodies (single-domain antibodies), and diabodies (bispecific/bivalent dimeric antibody fragments). In some embodiments, the antibodies are monoclonal antibodies. Monoclonal antibodies are antibodies that are secreted by a single B cell lineage. In some embodiments, the antibodies are polyclonal antibodies. Polyclonal antibodies are antibodies that are secreted by different B cell lineages. In some embodiments, the antibodies are chimeric antibodies. Chimeric antibodies are antibodies made by fusing the antigen binding region (variable domains of the heavy and light chains, VH and VL) from one species (e.g., mouse) with the constant domain from another species (e.g., human). In some embodiments, the antibodies are humanized antibodies. Humanized antibodies are antibodies from non-human species whose protein sequences have been modified to increase their similarity to antibody variants produced naturally in humans. In some embodiments, the antibodies are fusion antibodies (e.g., fusion of VHH or other antibody fragments to other protein types). In some embodiments, the antibody is a humanized NANOBODY® onto which CDR grafting may be performed.

Non-limiting examples of monoclonal antibodies produced by the methods provided herein include abciximab (REOPRO®), adalimumab (HUMIRA®), alefacept (AMEVIVE®), alemtuzumab (CAMPATH®), basiliximab (SIMULECT®), belimumab (BENLYSTA®), bezlotoxumab (ZINPLAVA®), canakinumab (ILARIS®), certolizumab pegol (CIMZIA®), cetuximab (ERBITUX®), daclizumab (ZENAPAX, ZINBRYTA®), denosumab (PROLIA, XGEVA®), efalizumab (RAPTIVA®), golimumab (SIMPONI®), inflectra (REMICADE®), ipilimumab (YERVOY®), ixekizumab (TALTZ®), natalizumab (TYSABRI®), nivolumab (OPDIVO®), olaratumab (LARTRUVO®), omalizumab (XOLAIR®), ozoralizumab, palivizumab (SYNAGIS®), panitumumab (VECTIBIX®), pembrolizumab (KEYTRUDA®), rituximab (RITUXAN®), tocilizumab (ACTEMRA®), trastuzumab (HERCEPTIN®), secukinumab (COSENTYX®), and ustekinumab (STELARA®).

In some embodiments, an antibody produced by the methods provided herein binds foreign antigen (e.g., pathogenic bacteria, viruses, and toxin proteins) or binds an antigen present on a host tissue (e.g., surface proteins present on epithelia or mucosal tissue or TNFα).

In some embodiments, an antibody produced by the methods provided herein binds specifically to a viral antigen. Non-limiting examples of viral antigens include Borrelia, Chagas, Chikungunya, Chlamydia, Cytomegalo, Dengue, Ebola, EBV, Encephalitis, Feline Leukemia Virus, Hantavirus, HBsAg, Hepatitis A, Hepatitis B, Hepatitis C, Hepatitis D, Hepatitis E, Herpes, HIV, HTLV, Influenza, Lassa, Malaria, Measles, Mumps, Mycoplasma, Norovirus, Papillomavirus, Parvovirus, Rubella, SARS, Shiga Like Toxin, Toxoplasma, Treponema, S. Typhi, Varicella, West Nile, and Zika antigens. In some embodiments, the antibody is an anti-HIV antibody selected from JM4VHH and VRC01scFV.

In some embodiments, the antibody produced binds specifically to a microbial antigen. Non-limiting examples of microbial antigens include *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., and *Lactobacillus* spp. antigens. In some embodiments, an antibody binds specifically to a bacterial toxin, such as shiga toxin, alpha toxin, anthrax toxin, cyanotoxin, diphtheria toxin, exotoxin, pertussis toxin, tetanus toxin, or botulinum neurotoxin.

In some embodiments, an antibody binds specifically to an inflammatory molecule, such as a cytokine. Non-limiting examples of cytokines include chemokines, interferons, interleukins, tumor necrosis factor, colony stimulating factor, TGF-beta superfamily. In specific embodiments, an antibody binds to TNF-alpha.

In some embodiments, the therapeutic protein is a cytokine. In some embodiments, the therapeutic protein is an anti-inflammatory cytokine. Non-limiting examples of anti-inflammatory cytokines include interleukin (IL)-1 receptor antagonist, IL-4, IL-6, IL-10, IL-11, and IL-13. In some embodiments, the therapeutic protein is IL-10.

In some embodiments, the therapeutic protein is an immunotherapeutic, onco-suppressive cytokine. Non-limiting examples of immunotherapeutic cytokines include IL-2, IL-7, IL-12, TGFβ, IFNγ, IFNα, and G-CSF.

In some embodiments, an artificial secretion peptide is fused to more than one heterologous protein (e.g., at least 2, at least 3, at least 4, at least 5, at least 10, at least 20, at least 30, at least 50, or at least 100 heterologous proteins), or a fragment (e.g., antibody fragment, such as an Fab, (Fab)$_2$, or Fc fragment). For example, an artificial secretion peptide may be fused to more than one therapeutic protein (e.g., the therapeutic proteins may be the same or different). In some embodiments, an artificial secretion peptide is fused to two or more heterologous proteins that are linked to each other through a linker (e.g. glycine-serine linker). In some embodiments, an artificial secretion peptide is fused to a cytokine that is linked to an antibody (or other antibody conjugate). In some embodiments, an artificial secretion peptide is fused to an IL10-IgFc fusion. In some embodiments, an artificial secretion peptide is fused to two cytokines (e.g. two IL-10 cytokines separated by a linker, such as a serine-glycine linker).

Advantageously, the artificial secretion signal peptides of the present invention enable production of antibodies of different molecular weights and also enable generation of multivalent antibodies. The present *Lactobacillus* system described herein is not limited by the size of antibody. For example, the artificial secretion signal peptides of the present invention may direct secretion of antibodies comprising one antibody domain (e.g. light chain variable domain and heavy chain variable domain). In some examples, the antibody comprises two antibody domains (e.g. two heavy chain variable domains, two light chain variable domains and a light chain variable domain and a heavy chain variable domain). In some examples, the antibody comprises three antibody domains. In some embodiments, an antibody of the present disclosure has one antigen binding site. In some embodiments, an antibody of the present disclosure includes two antigen-binding sites, for example, joined by a linker, such as a glycine-serine linker (a linker comprising glycine and serine). In some embodiments, an antibody of the present disclosure is a multivalent antibody comprising three, four, five, six, seven or eight antigen binding sites. In some embodiments, an antibody of the present disclosure includes three antigen-binding sites, for example, joined by two linkers (e.g. glycine-serine linkers).

Heterologous proteins produced herein are initially fused to an artificial secretion signal peptide, typically at the N-terminus of the protein, when expressed inside a *Lactobacillus* cell. It should be understood, however, that the signal peptide is cleaved before the mature protein is secreted from the cell. Thus, functional proteins produced and secreted by the methods provided herein should not include the artificial secretion signal peptide.

As shown in the Examples, the heterologous proteins produced as provided herein are functional. Proteins exported via the Sec translocase pathway are maintained in an unfolded state during synthesis and secretion, and only begin folding was the protein is released into the cell wall for diffusion into the extracellular environment. Thus, even if a protein is shown to be secreted, it bears no indication that it is correctly folded and functional. The heterologous proteins of the present disclosure were properly folded and functional. Methods for assessing the function of proteins, such as antibodies are known, any of which may be used as provided herein. For example, antibody function may be assessed by measuring the binding affinity of the antibody to the appropriate antigen, as shown in Example 1. In some embodiments, the binding affinity of an antibody produced by the methods provided herein (e.g., using an artificial secretion signal peptide in *Lactobacilli*) is comparable to or greater than the binding affinity of the same type of antibody produced using naturally-occurring secretion signal peptides.

Binding affinity is the apparent association constant or $K_A$. The $K_A$ is the reciprocal of the dissociation constant ($K_D$). The antibodies produce by the methods described herein may have a binding affinity ($K_D$) of at least $10^{-5}$, $10^{-6}$, $10^{-7}$, $10^{-8}$, $10^{-9}$, $10^{-10}$ M, or lower for a target antigen or antigenic epitope. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). In some embodiments, the antibodies described herein have a higher binding affinity (a higher $K_A$ or smaller $K_D$) to an appropriate antigen as compared to the binding affinity of the same type of antibody produced using naturally-occurring secretion signal peptides. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some embodiments, any of the antibodies produced as provided herein may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

[Bound]=[Free]/(*Kd*+[Free])

It is not always necessary to make an exact determination of $K_A$, though, since sometimes it is sufficient to obtain a quantitative measurement of affinity, e.g., determined using a method such as ELISA, FACS analysis or magnetic immunoprecipitation, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

Nucleic Acids

Provided herein, in some embodiments, are nucleic acids encoding a heterologous protein fused to an artificial secretion signal peptide. As described elsewhere herein, a nucleic acid encoding an artificial secretion signal peptide, in some embodiments, is at least 90% identical to the nucleic acid sequence identified by any one of SEQ ID NO:2, SEQ ID NO:4, or SEQ ID NO:6.

In some embodiments, the nucleic acid comprises a promoter operably linked to a nucleotide sequence encoding the protein. A promoter is a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. A promoter drives expression or drives transcription of the nucleic acid sequence that it regulates. A promoter is considered to be "operably linked" to a nucleotide sequence when it is in a correct functional location and orientation in relation to the nucleotide sequence to control ("drive") transcriptional initiation and/or expression of that sequence. Promoters may be constitutive or inducible. An inducible promoter is a promoter that is regulated (e.g., activated or inactivated) by the presence or absence of a particular factor.

Inducible promoters for use in accordance with the present disclosure include those that function in *Lactobacillus*. An exemplary inducible promoter for use herein is a tetracycline-inducible promoter.

Provided herein in, some embodiments, are expression vectors for expressing heterologous proteins in *Lactobacillus*. The expression vectors described herein may comprise any of the nucleic acids of the present disclosure. Examples of expression vectors include, but are not limited to, plasmids, phagemids and bacterial artificial chromosomes (BACs). The expression vectors of the present disclosure may be generated using standard molecular cloning methods (see, e.g., Current Protocols in Molecular Biology, Ausubel, F. M., et al., New York: John Wiley & Sons, 2006; Molecular Cloning: A Laboratory Manual, Green, M. R. and Sambrook J., New York: Cold Spring Harbor Laboratory Press, 2012; Gibson, D. G., et al., Nature Methods 6(5):343-345 (2009), the teachings of which relating to molecular cloning are herein incorporated by reference).

Methods of Heterologous Protein Production in Engineered *Lactobacillus* Cells

Some aspects of the present disclosure provide methods for producing a protein (e.g., a heterologous protein, such as a therapeutic protein) comprising culturing in cell culture media the engineered *Lactobacillus* cells as described herein to produce the protein. In some embodiments, the methods further comprise recovering (e.g., isolating and/or purifying) the protein from the cell culture media.

*Lactobacillus* cells as provided herein are engineered to include a nucleic acid encoding a heterologous protein fused to an artificial secretion signal peptide. Thus, the present disclosure provides *Lactobacillus* cells comprising a nucleic acid encoding a heterologous protein fused to an artificial secretion signal peptide and also provides *Lactobacillus* cells comprising the heterologous proteins. An engineered cell comprises at least one engineered nucleic acid or is otherwise structurally or functionally distinct from a wild-type counterpart. Thus, a *Lactobacillus* cell comprising an artificial secretion signal peptide is considered an engineered cell. In some embodiments, the engineered *Lactobacillus* cell comprises an expression vector of the present disclosure. Any of the nucleic acids of the present disclosure may be introduced into *Lactobacillus* cells using recombinant technology, including but not limited to bacterial transformation.

The *Lactobacillus* cells of the present disclosure may be propagated under conditions well known in the art (e.g. temperature, culture media and incubation times). In some embodiments, in which the *Lactobacillus* cells comprises nucleic acids operably linked to inducible promoters, the *Lactobacillus* cells are cultured in the presence of an effective amount inducing agent to induce expression from the inducible promoter. In some embodiments, the inducible promoter driving expression of a nucleic acid encoding a heterologous protein is a tetracycline-inducible promoter, thus, the *Lactobacillus* cells are cultured in an effective amount of tetracycline to induce expression from the tetracycline-inducible promoter.

Antibody purification methods include, but are not limited to, size exclusion chromatography, ammonium sulfate precipitation, ion exchange chromatography, immobilized metal chelate chromatography, thiophilic adsorption, melon gel chromatography and antibody ligand chromatography, any of which may be used as provided herein to recover a protein following secretion from *Lactobacillus* cells.

Surprisingly, use of the artificial secretion signal peptides of the present disclosure results in the production of heterologous proteins (e.g., production of antibodies) at a yield that is at least two orders of magnitude greater than heterologous proteins produced using naturally-occurring secretion signal peptides. In some embodiments, the yield of heterologous protein produced as provided herein is at least 2-10 orders of magnitude greater than heterologous proteins produced using naturally-occurring secretion signal peptides. For example, the yield of heterologous protein produced as provided may be 2, 3, 4, 5, 6, 7, 8, 9 or 10 orders of magnitude greater than heterologous proteins produced using naturally-occurring secretion signal peptides.

In some embodiments, the yield of heterologous protein produced as provided herein is at least 1 ng/mL of cell culture media (or other media or buffer). In some embodiments, the yield of heterologous protein produced is at least 1 ng/mL, at least 5 ng/mL, at least 10 ng/mL, at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 200 ng/mL, at least 300 ng/mL, at least 400 ng/mL, at least 500 ng/mL, at least 600 ng/mL, at least 700 ng/mL, at least 800 ng/mL, at least 900 ng/mL, or at least 1 µg/mL.

In some embodiments, the yield of heterologous protein produced as provided herein is at least 10 µg/mL of cell culture media (or other media or buffer). In some embodiments, the yield of heterologous protein produced is at least 20 µg/mL of cell culture media. In some embodiments, the yield of heterologous protein produced is at least 30 µg/mL of cell culture media. In some embodiments, the yield of heterologous protein produced is at least 40 µg/mL of cell culture media. In some embodiments, the yield of heterologous protein produced is at least 50 µg/mL of cell culture media. In some embodiments, the yield of heterologous protein produced is 10 µg/mL to 20 µg/mL, 10 µg/mL to 30 µg/mL, 10 µg/mL to 40 µg/mL, or 10 µg/mL to 50 µg/mL.

Also surprising is data provided herein that shows that cells of the *Lactobacillus* system as provided herein secrete heterologous proteins at greater quantities than *Escherichia* cells (see Example 3). Thus, in some embodiments, the methods provided herein, using *Lactobacillus* cells, result in heterologous protein production at yields that are at least 2-10 times greater than yields achieved when using *Escherichia* cells. For example, the methods provided herein, using *Lactobacillus* cells, may result in heterologous protein production at yields that are at least 2, 3, 4, 5, 6, 7, 8, 9 or 10 times greater than yields achieved when using *Escherichia* cells.

In some embodiments, the *Lactobacillus* cells of the present disclosure are probiotic cells. Probiotic cells, when administered in adequate amounts, confer a health benefit on the host to which they are administered. For example, the probiotic cells may confer a health benefit in the mucosa (e.g. gut and vaginal mucosa) of the host. Exemplary probiotic species of *Lactobacillus* include, but are not limited to, *L. gasseri*, *L. rhamnosus*, *L. plantarum*, *L. casei*, *L. salivarius* and *L. helveticus*. Exemplary *Lactobacillus* strains for use as provided herein include *L. rhamnosus* GG, *L. gasseri* ATCC 33323 and *L. gasseri* OLL2716.

In some instances, relative quantities of secreted proteins (e.g., antibodies) may be determined using enzyme-linked immunosorbent assay (ELISA) and Western blots (see, e.g., Examples 1 and 2 below). The function of secreted proteins may be tested using methods known in the art. For example, anti-HIV antibodies may be tested for their ability to bind gp120 (see, e.g., Example 1 below). Anti-HIV antibodies may also be tested for their ability to neutralize HIV with an TZM-bl assay (see, e.g., Example 2 below).

Therapeutic/Prophylactic Applications and Pharmaceutical Compositions

As discussed below, the antibody-secreting *Lactobacillus* cells of the present disclosure may be used as probiotic drug-delivery vectors in a variety of therapeutic and prophylactic applications. Engineered cells often run the risk of being recognized as foreign matter in a subject and could potentially elicit an adverse immune response. For example, certain types of bacteria are pathogenic (e.g. certain strains of *E. Coli* and *Staphylococcus aureus*). Therefore, even though *E. Coli* are amenable to genetic manipulation, they are not favorable drug-delivery vectors in subjects (e.g. humans). Advantageously, various strains of *Lactobacillus* have been categorized as Generally Recognized as Safe (GRAS) by the Federal Drug Administration (FDA) and thus, may be favorable agents for drug delivery. Furthermore, while genome editing technologies, such as CRISPR, can have off target effects that permanently introduce unintended mutations, the *Lactobacillus* system of the present disclosure enables localized drug delivery to mucosal organs, prolonged half-life via continuous production by colonizing microbes and lower production costs.

The present disclosure also provides, in some aspects, methods that include administering to a subject the engineered *Lactobacillus* cells (e.g., probiotic cells) or therapeutic proteins (e.g., an inflammatory agent, an anti-inflammatory agent, an immunomodulatory agent, an anti-cancer agent, a metabolic agent, an antiviral/virocidal agent, or an antibacterial/bacteriocidal agent) of the present disclosure.

Administration of any of the engineered *Lactobacillus* cells (e.g., probiotic cells) or therapeutic proteins of the present disclosure may increase the amount of a particular protein in a subject by at least 5% (e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, at least 100%, at least 200%, at least 300%, at least 400%, at least 500%, at least 600%, at least 700%, at least 800%, at least 900%, or at least 1,000%) as compared to the baseline levels of the protein in a subject. In some embodiments, administration of any of the engineered *Lactobacillus* cells (e.g., probiotic cells) of the present disclosure results in the production of a heterologous protein in a subject that is at least 2 times, 5 times, 10 times, 20 times, 30 times, 40 times, 50 times, 60 times, 70 times, 80 times, 90 times, or 100 times greater than the amount of the protein produced under control conditions.

The amount of a protein (e.g., a heterologous protein, including a therapeutic protein) in a subject may be measured in any tissue or organ (e.g., blood, colon, lung, heart, mucus, sweat, semen, saliva, etc.) using any suitable method (e.g., western blot, immunofluorescence with an antibody that recognizes the protein of interest, or ELISA). The amount of a protein may be measured following at least one dose (e.g., at least 2, 3, 4, 5, 6, 7, 8, 9, 10, 20, 50, or 100 doses) of any of the engineered *Lactobacillus* cells (e.g., probiotic cells) or therapeutic proteins of the present disclosure and compared with the baseline or control levels of the protein.

The baseline levels or control levels of a protein may refer to the amount of the endogenous protein prior to administration of any of the engineered *Lactobacillus* cells (e.g., probiotic cells) or therapeutic proteins of the present disclosure. As a non-limiting example, the control or baseline levels of a protein may be determined within 1 month, 2 months, 3 months, 4 months, 5 months, 10 months, or 12 months prior to the administration of any of the engineered *Lactobacillus* cells (e.g., probiotic cells) or therapeutic proteins of the present disclosure.

Typically, the subject is a human subject. In some embodiments, the subject has an autoimmune condition. Non-limiting examples of autoimmune conditions include Addison's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis, Myasthenia gravis, Myositis, Narcolepsy, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Wegener's granulomatosis (or Granulomatosis with Polyangiitis (GPA)).

The present disclosure provides, in some embodiments, methods of administering to a subject with gut inflammation the engineered *Lactobacillus* cells or the secreted therapeutic proteins. Examples of gut inflammation include, but are not limited to, Crohn's disease, irritable bowel disease (IBD), irritable bowel syndrome (IBS) and ulcerative colitis. Ulcerative colitis, for example, causes long-lasting inflammation and sores (ulcers) in the innermost lining of the large intestine (colon) and rectum. Crohn's disease, as another example, is characterized by inflammation of the lining of the digestive tract, which often spreads deep into affected tissues.

In some embodiments, the engineered *Lactobacillus* cells secreting anti-inflammatory cytokines (e.g. anti-TNFα) of the present disclosure are administered to a subject with gut inflammation. In some embodiments, the gut inflammation is Crohn's disease. In some embodiments, the gut inflammation is irritable bowel disease. In some embodiments, the gut inflammation is irritable bowel syndrome. In some embodiments, the gut inflammation is ulcerative colitis. In some embodiments, administration of the engineered *Lactobacillus* may reduce inflammation of a subject at least 10% (e.g. 15%, 20%, 25%, 30%, 35%, 40%, 45%, 55%, 60%, 70%, 80% or 90%) Inflammation may be monitored using methods well-known in the art. For example, levels of inflammatory cytokines may be detected using an enzyme-linked immunosorbent assay (ELISA).

In some embodiments, the subject has a viral infection or a microbial infection. The viral infection or microbial infection may affect any tissue or organ, including the gut, skin, lung, nasopharynx, or female genital tract. Examples of viral infections include, but are not limited to Borrelia, Chagas, Chikungunya, Chlamydia, Cytomegalo, Dengue, Ebola, EBV, Encephalitis, Feline Leukemia Virus, Hantavirus, HBsAg, Hepatitis A, Hepatitis B, Hepatitis C, Hepatitis D, Hepatitis E, Herpes, HIV, HTLV, Influenza, Lassa, Malaria, Measles, Mumps, Mycoplasma, Norovirus, Rotovirus, Papillomavirus, Parvovirus, Rubella, SARS, Shiga Like Toxin, Toxoplasma, Treponema, S. Typhi, Varicella, West Nile, and Zika. Examples of microbial infections include, but are not limited to, *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., and *Lactobacillus* spp. infection.

In some embodiments, a *Lactobacillus* cell composition is administered to a subject as a preventative measure, for example, to prevent a microbial infection or a viral infection, such as an HIV infection. Thus, in some embodiments, the *Lactobacillus* cells are engineered to encode a nucleic acid encoding an anti-microbial antibody or an anti-viral antibody, such as an anti-HIV antibody.

In some embodiments, any of the engineered *Lactobacillus* cells (e.g., *L. gasseri, L. rhamnosus, L. plantarum, L. casei, L. salivarius, L. acidophilus, L. delbreuckii, L. bulgaricus, L. jensenii, L. crispatus, L. paracasei, L. johnsonii, L. reuteri, L. fermentum, L. brevis*, and *L. helveticus*) of the present disclosure that produce one or more heterologous proteins are administered to a subject that has a disease (e.g., a disease affecting the gastrointestinal tract, respiratory tract, female genital tract, or any combination thereof). The engineered *Lactobacillus* cells may modulate host tissue (e.g., immunomodulatory effects via IL10 or hormonal effects via GLP1) or to neutralize pathogens or toxins (e.g. virus or bacteria). As a non-limiting example, *Lactobacillus* cells engineered to secrete hBD1, J3, anti-shiga toxin nanobodies, or a combination thereof may be administered to a subject in need thereof to neutralize a pathogen, a toxin, or any combination thereof.

The *Lactobacillus* cells and/or secreted proteins, in some embodiments, are formulated in a pharmaceutical composition. The pharmaceutical composition may include a pharmaceutical carrier (e.g. liposome or nanocarrier). The pharmaceutical composition may also include, or may alternatively include, a pharmaceutically-acceptable excipient. Non-limiting examples of pharmaceutically-acceptable excipients include water, saline, dextrose, glycerol, ethanol and combinations thereof. The pharmaceutically-acceptable excipient may comprise phosphate buffered saline, a bicarbonate solution, a preservative, a stabilizing agent, an emulsifier (e.g. a phospholipid emulsifier), a solubilizing agent (e.g., surfactant), or a binding agent. The excipient may be selected on the basis of the mode and route of administration, and standard pharmaceutical practice.

General considerations in the formulation and/or manufacture of pharmaceutical compositions of the present disclosure, may be found, for example, in Remington: The Science and Practice of Pharmacy 21st ed., Lippincott Williams & Wilkins, 2005 (incorporated herein by reference in its entirety).

An effective amount or a therapeutically effective amount is an amount of an active agent required to confer a therapeutic effect on a subject, either alone or in combination with at least one other active agent. Effective amounts vary, as recognized by those skilled in the art, depending on the route of administration, excipient usage, and co-usage with other active agents. The quantity to be administered depends on the subject to be treated, including, for example, the strength of an individual's immune system or genetic predispositions. Suitable dosage ranges are readily determinable by one skilled in the art and may be on the order of micrograms of the polypeptide of this disclosure. The dosage of the compositions disclosed herein may depend on the route of administration and varies according to the size of the subject.

In some instances, at least one dose (e.g., at least 2, 3, 4, 5, 6, 7, 8, 9, 10, 20, 50, or 100 doses) of any of the engineered *Lactobacillus* cells (e.g., probiotic cells) or therapeutic proteins is administered to a subject. As an example, a dose of engineered *Lactobacillus* cells may comprise $10^3$ to $10^{50}$ (e.g., $10^6$ to $10^{20}$) colony-forming units (CFUs).

As will be appreciated by one of ordinary skill in the art, dosing schedules may vary depending on a variety of factors (e.g., the type of composition to be administered, including the type or strain of bacteria to be administered, the type of protein to be administered, etc.). Non-limiting examples of dosing schedules include administration of at least one dose a day, at least one dose every other day, at least two doses a day, at least three doses a day, at least one dose every two days, at least one dose every three days, at least one dose every four days, at least one dose every 5 days, at least one dose every six days, at least one dose every week, or at least one dose every month. In some embodiments, at least one dose (e.g., one dose or three doses) of any of the engineered *Lactobacillus* cells is administered to a subject once a day, once every other day, or once a week. Doses of any of the engineered Lactobacillus cells or proteins described herein may be administered with a meal or administered without a meal.

Suitable routes of administration include parenterally, by injection or implantation subcutaneously, intravenously, intramuscularly, intrathecally, intraperitoneally, intracuteanously, intrasternally, intraarticularlly, intracranially, intralesionally, intrarectually, intrarectally, intravaginally, intranasally, intragastically, intratracheally, or intrapulmonarily. Alternatively, other modes of administration including suppositories, oral formulations, enteral, nasal, topical or transmucosal administration may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions may take the form of solutions, suspensions, tablets, pills, capsules, sustained release formulations or powders. As a non-limiting example, *Lactobacillus* cells may be formulated in enteric capsules, tablets, a slurry, or in a dairy based food product.

It will be appreciated by one of ordinary skill in the art that a suitable route of administration may depend on the type of composition to be administered. For example, certain routes of administration (e.g., parenteral, intravenous, or subcutaneous administration) may not be suitable for administration of bacterial cells to a subject because, without being bound by a particular theory, direct administration of bacteria into the blood stream may cause sepsis. In contrast, parenteral, intravenous, or subcutaneous administration may be suitable for administration of a recombinant peptide produced by any of the methods described herein.

As mentioned above, the dosage required depends on the choice of the route of administration; the nature of the formulation; the nature of the subject's illness; the subject's species, size, weight, surface area, age, and sex; other drugs being administered; and the judgment of the practitioner. Suitable dosages are in the range of 0.01-100.0 mg/kg. Wide variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

In some embodiments, method provided herein include computing a *Lactobacillus* strain-specific signal peptide sequence using amino acid residue position weight matrices (see, e.g., Example 1 below). An exemplary computer program that may be used to compute position weight matrices is GLAM. In some embodiments, the methods include computing the position weight matrices and further using an algorithm that enables predictive scoring of SP function to filter potentially nonfunctional variants in silico (see, e.g., Example 4 below).

Additional Embodiments

The present disclosure also provides the following additional embodiments encompassed by numbered paragraphs.

1. An artificial secretion signal peptide comprising an amino acid sequence that is at least 90% identical to an amino acid sequence selected from the group consisting of SEQ ID NO:1, SEQ ID NO:3, SEQ ID NO:5, SEQ ID NO: 11, and SEQ ID NO:7.

2. The artificial secretion signal peptide of paragraph 1, wherein the amino acid sequence is at least 95% identical to the amino acid sequence identified by SEQ ID NO:1.

3. The artificial secretion signal peptide of paragraph 2, wherein the amino acid sequence is at least 98% identical to the amino acid sequence identified by SEQ ID NO:1.

4. The artificial secretion signal peptide of paragraph 3, wherein the amino acid sequence is identical to the amino acid sequence identified by SEQ ID NO:1.

5. The artificial secretion signal peptide of paragraph 1, wherein the amino acid sequence is at least 95% identical to the amino acid sequence identified by SEQ ID NO:3.

6. The artificial secretion signal peptide of paragraph 5, wherein the amino acid sequence is at least 98% identical to the amino acid sequence identified by SEQ ID NO:3.

7. The artificial secretion signal peptide of paragraph 6, wherein the amino acid sequence is identical to the amino acid sequence identified by SEQ ID NO:3.

8. The artificial secretion signal peptide of paragraph 1, wherein the amino acid sequence is at least 95% identical to the amino acid sequence identified by SEQ ID NO:5.

9. The artificial secretion signal peptide of paragraph 8, wherein the amino acid sequence is at least 98% identical to the amino acid sequence identified by SEQ ID NO:5.

10. The artificial secretion signal peptide of paragraph 9, wherein the amino acid sequence is identical to the amino acid sequence identified by SEQ ID NO:5.

11. The artificial secretion signal peptide of paragraph 1, wherein the amino acid sequence is at least 95% identical to the amino acid sequence identified by SEQ ID NO: 11 or SEQ ID NO:7.

12. The artificial secretion signal peptide of paragraph 11, wherein the amino acid sequence is at least 98% identical to the amino acid sequence identified by SEQ ID NO: 11 or SEQ ID NO:7.

13. The artificial secretion signal peptide of paragraph 12, wherein the amino acid sequence is identical to the amino acid sequence identified by SEQ ID NO: 11 or SEQ ID NO:7.

14. A protein fused to the artificial secretion signal peptide of any one of paragraphs 1-13.

15. The protein of paragraph 14, wherein the artificial secretion signal peptide is fused to the N-terminus of the protein.

16. The protein of paragraph 14 or 15, wherein the protein is a therapeutic protein.

17. The protein of paragraph 16, wherein the protein is an antibody.

18. The protein of paragraph 17, wherein the antibody binds specifically to a viral antigen or a microbial antigen.

19. The protein of paragraph 17 or 18, wherein the antibody is a single-domain antibody (NANOBODY®).

20. The protein of paragraph 16, wherein the therapeutic protein is a cytokine.

21. The protein of paragraph 20, wherein the cytokine is IL-10.

22. A nucleic acid encoding the artificial secretion signal peptide of any one of paragraphs 1-15 or the protein of any one of paragraphs 14-21.

23. The nucleic acid of paragraph 22, wherein the nucleic acid comprises a promoter operably linked to a nucleotide sequence encoding the protein.

24. The nucleic acid of paragraph 23, wherein the promoter is an inducible promoter.

25. The nucleic acid of any one of paragraphs 22-24, wherein the nucleic acid is codon-optimized.

26. A vector comprising the nucleic acid of any one of paragraph 22-25.

27. The vector of paragraph 26, wherein the vector is an expression vector.

28. An engineered *Lactobacillus* cell comprising the nucleic acid of any one of paragraphs 22-25 or the vector of paragraph 26 or 27.

29. The engineered *Lactobacillus* cell of paragraph 28, wherein the engineered Lactobacillus cell is selected from *L. gasseri* and *L. rhamnosus* cells.

30. A method for producing a protein comprising culturing in cell culture media the engineered *Lactobacillus* cell of paragraph 28 or 29 to produce the protein encoded by the nucleic acid.

31. The method of paragraph 30, wherein the engineered *Lactobacillus* cell is a *Lactobacillus rhamnosus* GG (LGG) cell.

32. The method of paragraph 30 or 31, wherein the *Lactobacillus* cell produces at least 10 µg of the protein per mL of cell culture media.

33. The method of paragraph 32, wherein the *Lactobacillus* cell produces at least 30 µg of the protein per mL of cell culture media.

34. The method of paragraph 33 further comprising recovering the protein from the cell culture media.

35. A protein produced by the method of paragraph 33 or 34.

36. A method comprising administering to a subject the engineered *Lactobacillus* cell of paragraph 28 or 29 or the protein of paragraph 35.

37. The method of paragraph 36, wherein the subject has an autoimmune condition.

38. The method of paragraph 37, wherein the autoimmune condition is inflammatory bowel disease or Crohn's disease.

39. The method of paragraph 36, wherein the subject has a viral infection or a microbial invention.

40. A method, comprising:
(a) computing an amino acid residue position weight matrix (PWM) for a population of signal sequences within a library of bacterial strain-specific sequences; and
(b) generating a consensus signal peptide sequence based on the PWM for the population of signal sequences.

41. The method of paragraph 40 further comprising (c) expressing in cells of the bacterial strain a heterologous protein of interest linked to a signal peptide comprising the consensus signal peptide sequence.

42. The method of paragraph 40 or 41, wherein the bacterial strain is selected from a strain of *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp.

43. The method of paragraph 42, wherein the bacterial cells are probiotic cells.

44. The method of any one of paragraphs 40-43, wherein the heterologous protein of interest is a therapeutic protein.

45. The method of paragraph 44, wherein the therapeutic protein is an antibody.

46. The method of any one of paragraphs 41-45, wherein the nucleic acid encoding the heterologous protein of interest linked to the consensus signal peptide sequence is operably linked to an inducible promoter.

EXAMPLES

Example 1

Identification of Artificial Secretion Signals Capable of Secreting Antibody Fragments from *Lactobacillus*

To identify signal peptide sequences capable of secreting various antibody fragments reliably and reproducibly, a high-throughput screen of a pan-genomic library of secretion signals assembled from computational analyses of all *Lactobacilli* with sequenced genomes was conducted. While this constitutes the largest candidate secretion signal peptide pool to date that expands the range to which the genetic dial may be turned to improve secretion, it also provided a basis for a parallel approach: rather than rely on preexisting secretion signals which presumably co-evolved with their natural protein partners, the library can be compressed into template sequences for the design of artificial signals that are potentially generalizable on a strain-by-strain basis. A publically available motif discovery algorithm was used to analyze strain-specific subsections of the library to compute amino acid residue position weight matrices (PWM) and generate maximum probability peptides.

Figure 1B:
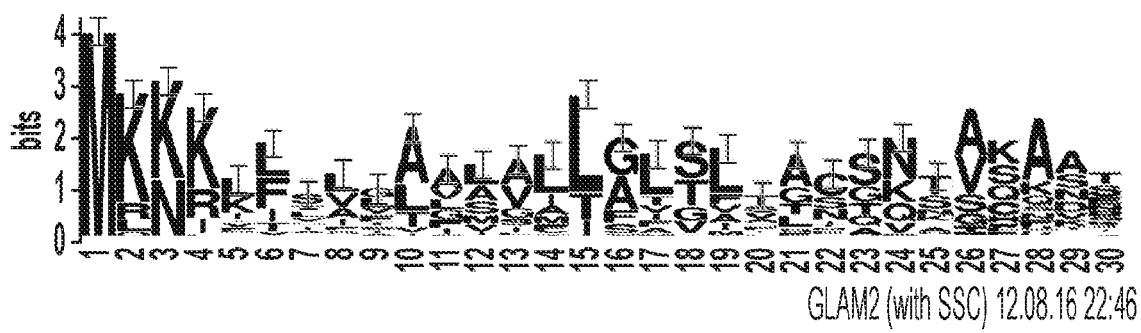
Figure 1C:
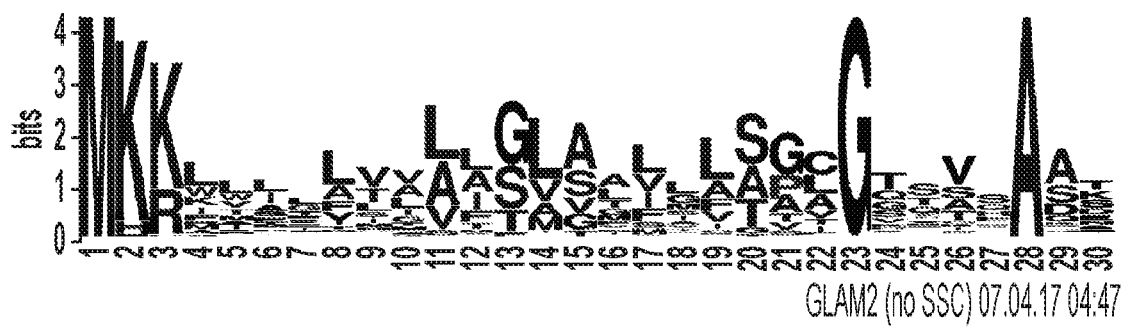
Figures 2A, 2B:
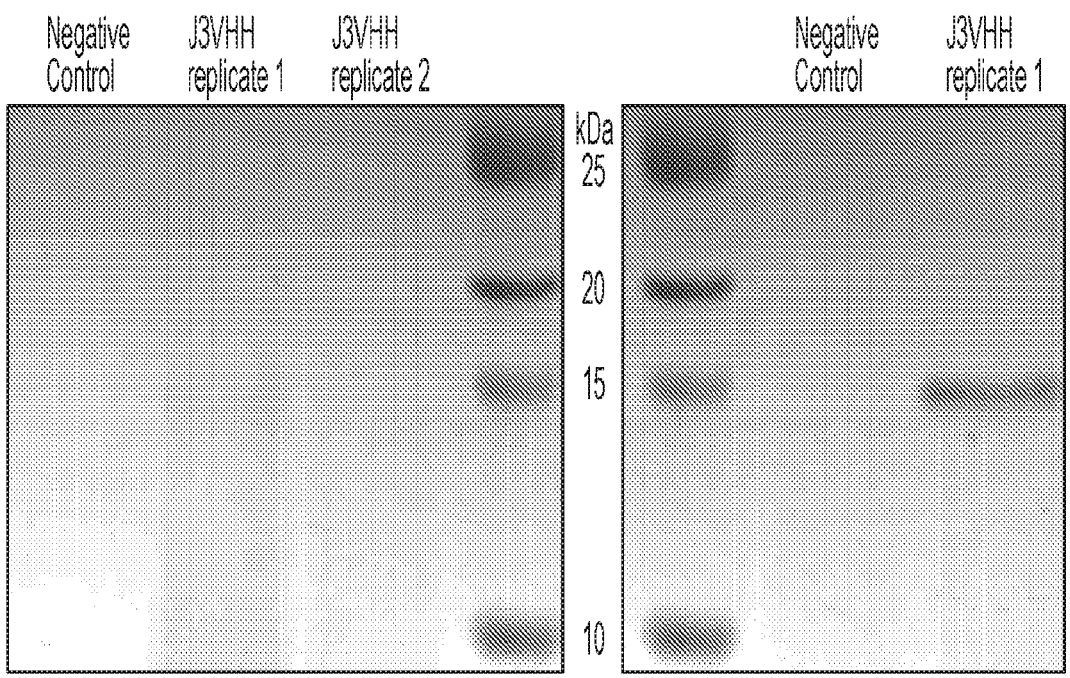
FIG. 2 shows data indicating that artificial secretion signal peptides are capable of promoting secretion of an anti-HIV antibody fragment (J3VHH) from *Lactobacillus*. Purified culture supernatant was analyzed. The expected size of J3VHH is 14.3 KDa. Coomasie stain of his-purified culture supernatant (SimplyBlue by Invitrogen) was used to produce these images. Panel A: shows data indicating the presence of J3VHH in purified culture supernatant from *L. rhamnosus* transformed with vector encoding the secretion signal peptide provided as SEQ ID NO: 1 fused to J3VHH. Molecular weight protein markers are indicated in the last lane. Panel B: shows data indicating the presence of J3VHH in purified culture supernatant from *L. gasseri* transformed with vector encoding SEQ ID NO:3 fused to J3VHH. Molecular weight markers are indicated in the first lane.

Since *L. rhamnosus* GG and *L. gasseri* are noteworthy probiotics in the human microbiome (e.g., in gut and vaginal mucosa) and may be used in endpoint applications in the human microbiome, analysis of peptide sequences was performed on *L. rhamnosus* GG (FIG. 1, panel A) and *L. gasseri* (FIG. 1, panel B). The highest probability sequence yielded by each strain's PWM (SEQ ID NO: 1 for *L. rhamnosus* GG and SEQ ID NO: 3 for *L. gasseri*) was first selected and the corresponding strain-specific and codon-optimized nucleotide sequence (SEQ ID NO: 2 for *L. rhamnosus* GG and SEQ ID NO: 4 for *L. gasseri*) was generated using codon-use tables made from the species genome. Then, the ability of each secretion signal peptide to direct secretion when N-terminally fused to an anti-HIV antibody fragment[1] (J3VHH) was tested. Remarkably, both artificial signal peptides directed the secretion of J3VHH (FIG. 2, panels A and B).

To date, no naturally occurring secretion signal capable of secreting nanobodies in *L. gasseri* have been found. For *L. rhamnosus*, the disclosed secretion signal peptide outperforms the highest yield naturally occurring sequence by two orders of magnitude. Secretion was further confirmed by mass spectrometry, with 22.05% and 59.84% protein coverage for *L. rhamnosus* and *L. gasseri*, respectively (the difference in coverage correlates to the relative secretion yields as seen in FIG. 2). Additionally, when the secretion signal peptide is not matched to the strain the sequence was computed for, no secretion was observed, indicating the strain-specificity of this strategy. It is also noteworthy that when these sequences are expressed by a constitutive promoter, the signal peptides rapidly mutate in a manner that breaks their function. However, when controlled by a tetracycline-inducible system, they remain genetically stable.

Figure 3:
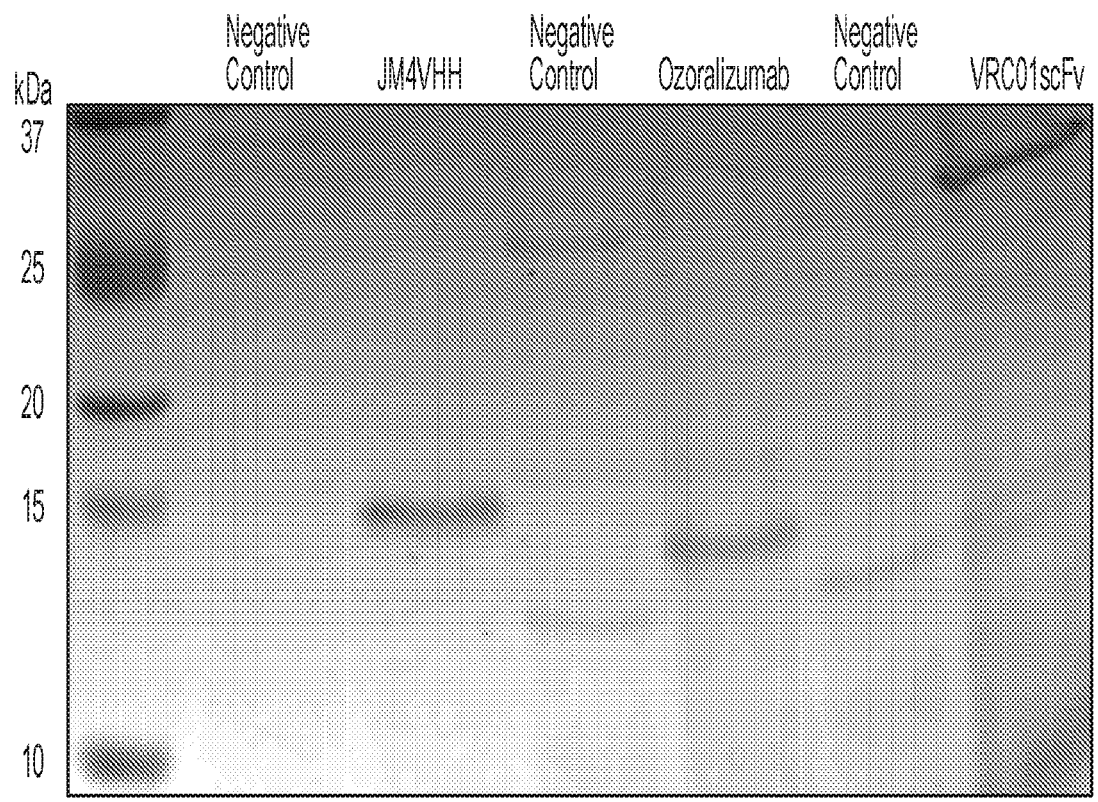
FIG. 3 shows data indicating that the secretion signal with the sequence provided in SEQ ID NO:3 is capable of promoting secretion of JM4VHH (an anti-HIV antibody fragment), ozoralizumab (an anti-TNFα antibody fragment) and VRC01scFV (an anti-HIV antibody fragment derived from the broadly neutralizing IgG antibody VRC01) from *Lactobacillus*. Purified culture supernatant from *L. gasseri* transformed with vector encoding secretion signal provided in SEQ ID NO: 3 fused to the indicated antibody fragments. Molecular weight markers are indicated in the first lane. The expected size for each antibody fragment is as follows: JM4VHH: 15 kDa, ozoralizumab: 13.3 kDa and VRC01scFV: 28.8 kDa. Coomasie stain of his-purified culture supernatant (SimplyBlue by Invitrogen) was used to produce these images.

The disclosed secretion signal peptides also functioned with other antibodies fragments, including a second, published anti-HIV NANOBODY®[2] (JM4VHH), an anti-TNFα NANOBODY® marketed by Ablynx (ozoralizumab), and a published, anti-HIV single chain fragment[3] derived from the broadly neutralizing IgG antibody VRC01 (VRC01scFv). Secretion into supernatant by *L. gasseri* when fused to the secretion signal peptide provided as SEQ ID NO: 3 was detected at equal levels to J3VHH in the case of JM4VHH and ozoralizumab, and at half that level for VRC01scFv (FIG. 3). The reduced yield for the latter protein may be attributable to the fact that it is twice the size of the other antibody fragments tested.

The antibody fragments secreted from *Lactobacillus* using the disclosed secretion signal peptides were tested to determine whether the antibody fragments were functional. Proteins exported via the Sec translocase pathway are maintained in an unfolded state during synthesis and secretion, and only begin folding was the protein is released into the cell wall for diffusion into the extracellular environment. Thus, even if a protein is shown to be secreted, it bears no indication that it is correctly folded and functional. As such, assays that measure binding affinity to the appropriate antigens were used to determine whether the secreted antibody fragments were functional.

Figure 4:
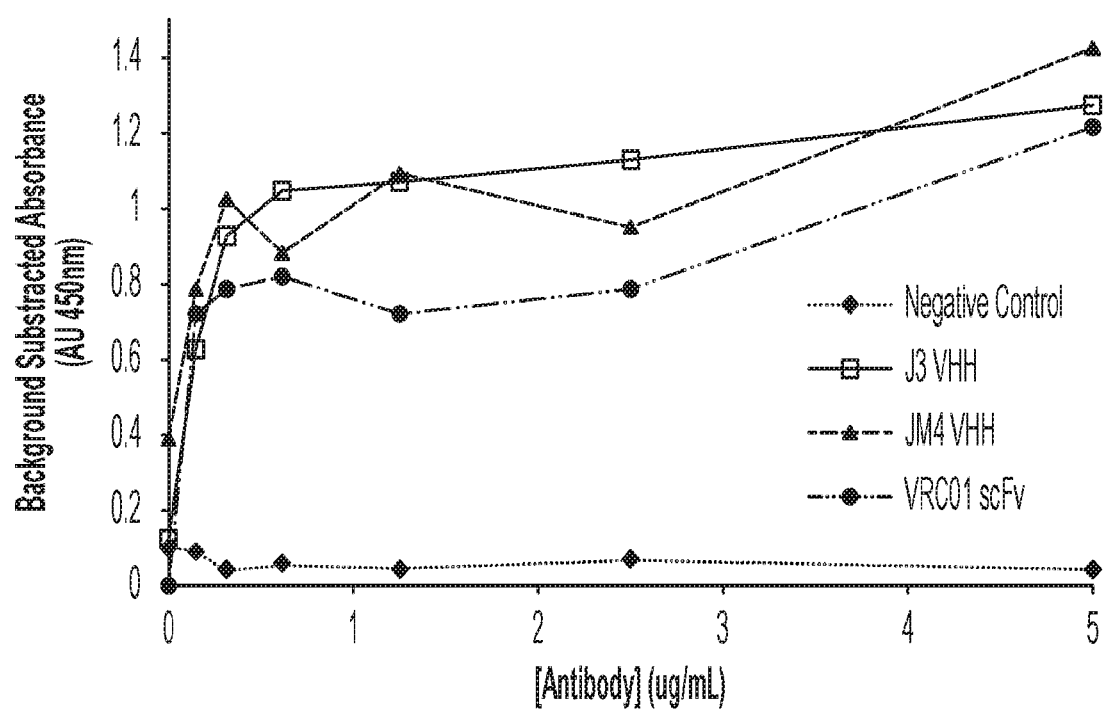
FIG. 4 shows data indicating that a secretion signal with the sequence provided in SEQ ID NO:3 is capable of secreting functional antibody fragments from *L. gasseri*. Data was generated using an Enzyme-linked immunosorbent assay (ELISA) to measure the binding affinity of indicated secreted antibodies for gp120 (strain YU2).
Figure 7:
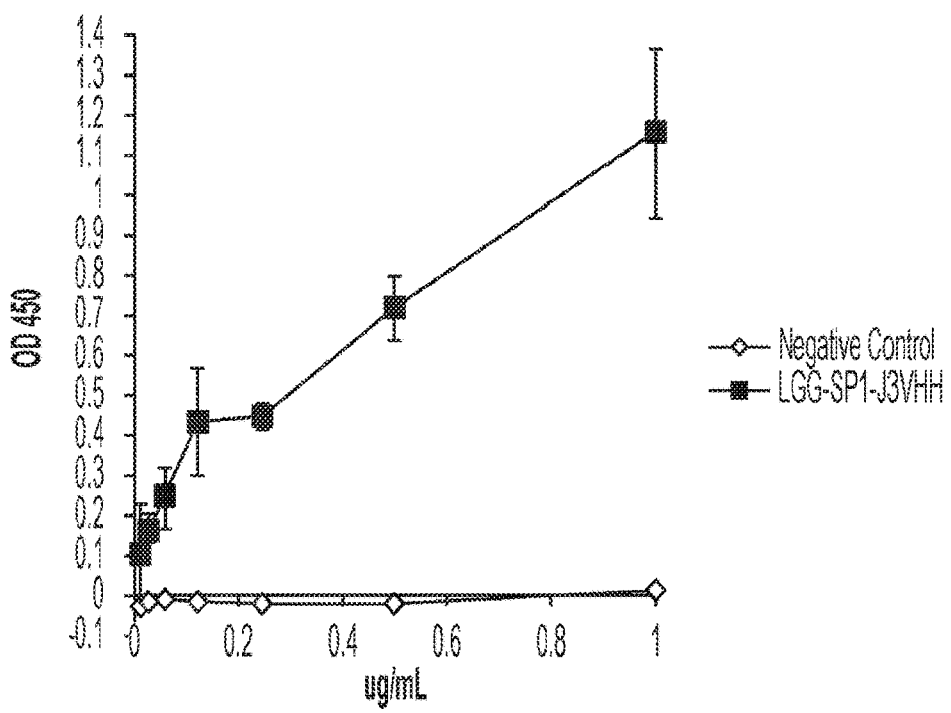
FIG. 7 shows data indicating that *L. rhamnosus* GG SP1 (SEQ ID NO: 1) secretes functional J3VHH from *L. rhamnosus* capable of binding gp120. The results of an ELISA assay that detects binding to gp120 is shown.
Figure 11:
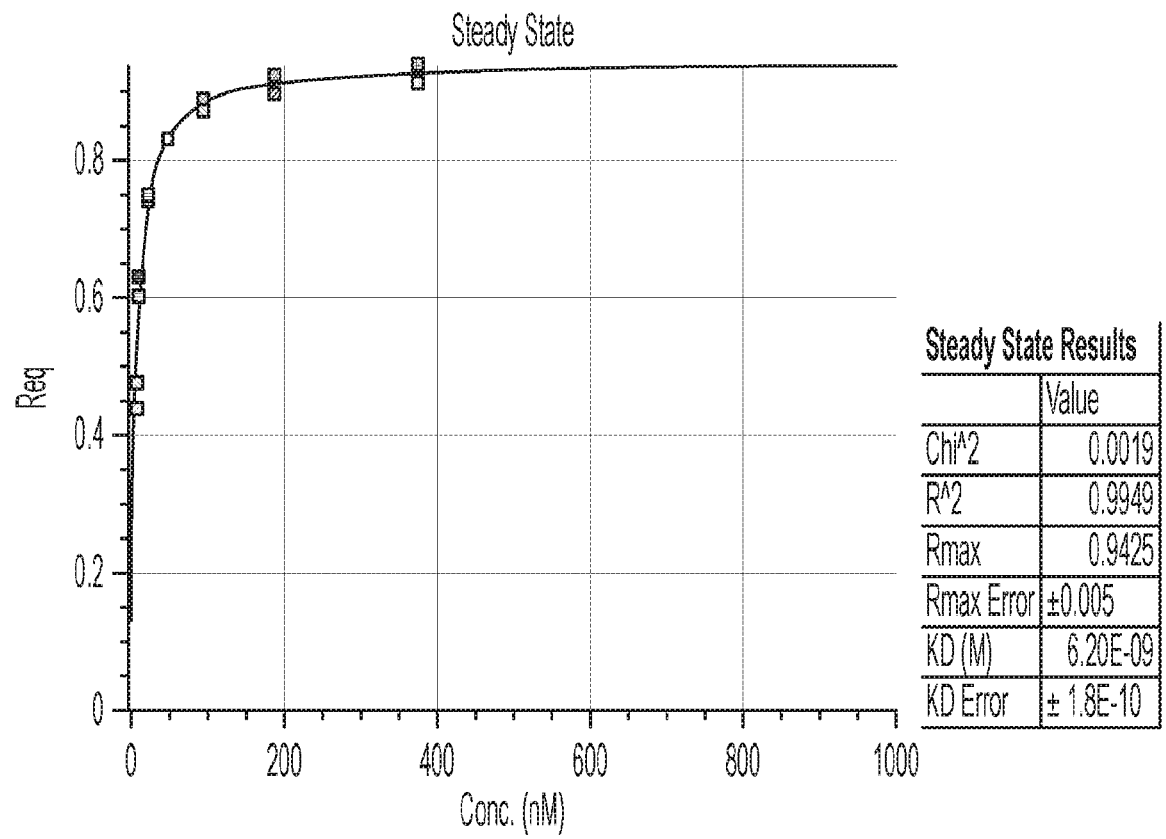
FIG. 11 includes data analyzing the function of the anti-TNFα antibody fragment marketed by Ablynx, Ozoralizumab, secreted by *L. rhamnosus* GG SP1 (SEQ ID NO: 1), via biolayer interferometry. The $K_D$ for two replicates is shown.

As such, the antibody fragments were verified to be properly folded by being tested directly for function, using assays that measure binding affinity to the appropriate antigens. All of the anti-HIV antibodies tested were documented to bind gp120—the viral coat protein that coordinates binding to T-cell CD4 receptors. Accordingly, an enzyme-linked immunosorbent assay (ELISA) was performed to measure antibody binding affinity for gp120 (FIG. 4) in *L. gasseri* comprising antibody fragments N-terminally fused to a secretion signal with the amino acid sequence provided in SEQ ID NO: 3. The binding curves measured for all anti-HIV antibody variants are comparable to the previously published results for each[1-3]. Function was secondarily verified by biolayer interferometry, using an Octet instrument to measure binding kinetics in real time. These experiments corroborated the ELISA data for tested anti-HIV antibodies, reporting $K_D$ values for HIV-RSC3 of 10.22 nM, 75.55 nM, and 110.9 nM for VRC01scFV, J3VHH, and JM4VHH, respectively. It is worth noting that J3VHH and JM4VHH are documented to have relatively weaker binding to the RSC3 antigen as compared to other antibody variants, such as VRC01). In parallel, *L. gasseri* secreted ozoralizumab binding against TNFα was measured to have a $K_D$ of 0.69 nM±0.26 nM (n=3). In both instances, antibodies with no expected binding activity were used as negative controls (i.e., J3VHH for TNFα experiments, ozoralizumab for HIV experiments). Negative controls registered no measurable binding activity across all validation experiments. Similarly, the artificial secretion signal comprising *L. rhamnosus* GG SP1 (SEQ ID NO: 1) secreted functional J3VHH as determined by the gp120 ELISA assay described above (FIG. 7). The function of the anti-TNFα antibody fragment marketed by Ablynx, ozoralizumab, secreted by *L. rhamnosus* GG SP1 was measured via biolayer interferometry. This method showed that the secreted antibody fragment bound to its target protein with nanomolar affinity ($K_D$=6.2 nM, 2 replicates) on par with the ozoralizumab activity reported by Ablynx (FIG. 11).

Figure 5:
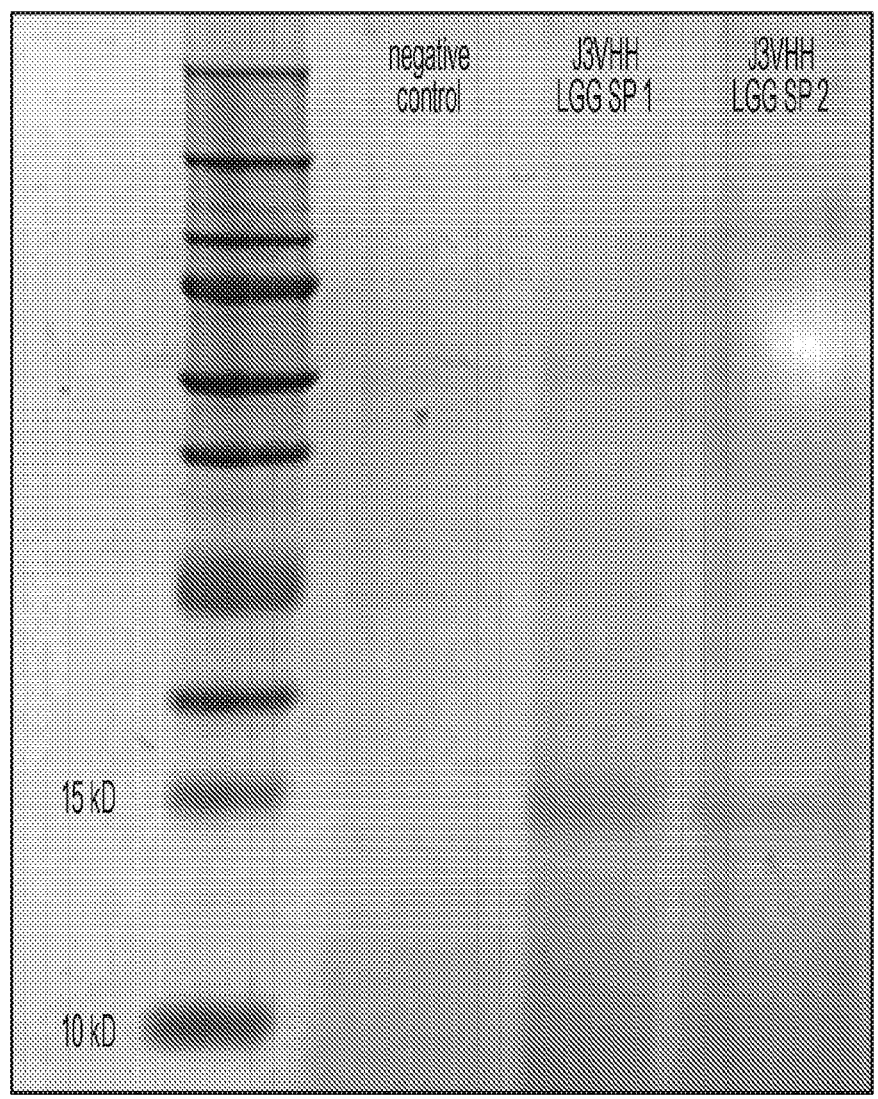
FIG. 5 shows data indicating that *L. rhamnosus* GG (LGG) SP1 (SEQ ID NO: 1) and *L. rhamnosus* GG SP2 (SEQ ID NO:5) are capable of secreting J3VHH. The predicted size of J3VHH is 14.3 kDa. Coomasie stain of his-purified culture supernatant (SimplyBlue by Invitrogen) was used to produce these images.
Figure 6:
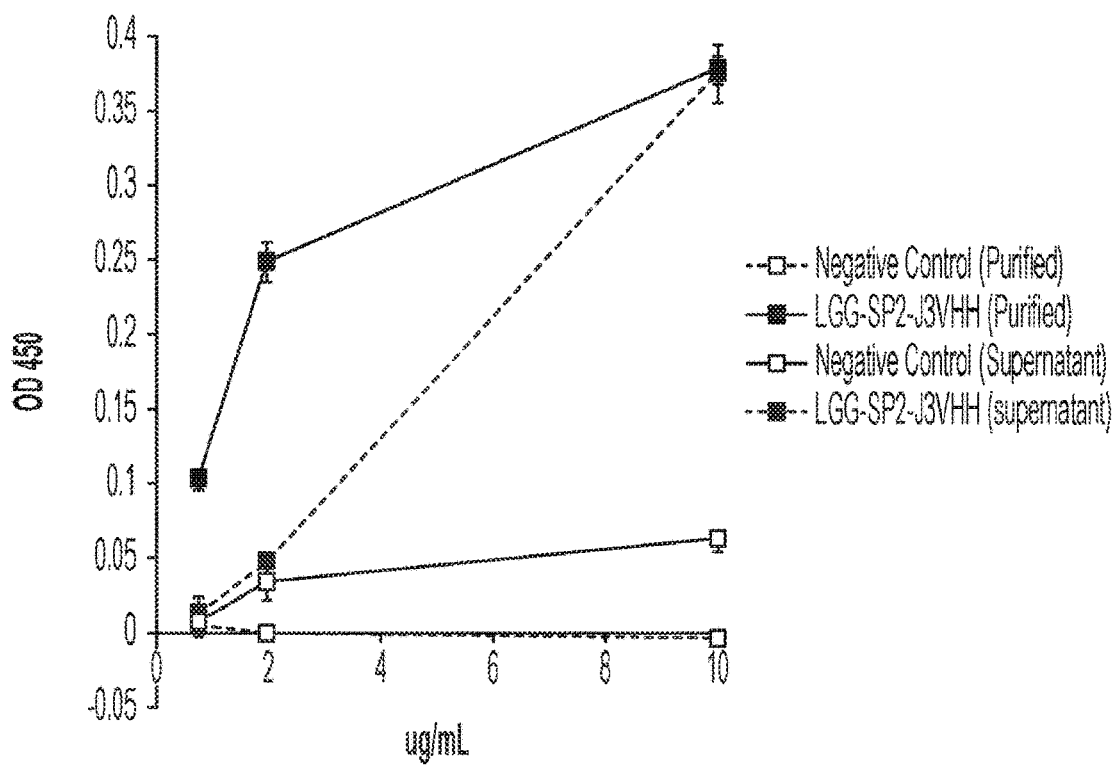
FIG. 6 shows data indicating that *L. rhamnosus* GG SP2 (SEQ ID NO: 5) secretes functional J3VHH from *L. rhamnosus* capable of binding gp120. The results of an ELISA assay that detects binding to gp120 is shown.

Another secretion signal peptide with reproducible functionality in *L. rhamnosus* GG was identified with the amino acid sequence provided in SEQ ID NO: 5 (*L. rhamnosus* GG SP2) based on another sequence of different length (30 amino acids for *L. rhamnosus* GG SP2 versus 25 amino acids for *L. rhamnosus* GG SP1). A nucleic acid encoding SEQ ID NO: 5 is provided as SEQ ID NO: 6. Both *L. rhamnosus* GG SP1 and *L. rhamnosus* GG SP2 secreted J3VHH from *L. rhamnosus* (FIG. 5). An ELISA was performed to measure whether the J3VHH secreted by *L. rhamnosus* GG SP2 was functional. Supernatant and purified supernatant from engineered *L. rhamnosus* GG comprising *L. rhamnosus* GG SP2 fused to J3VHH was analyzed to determine the binding affinity of the secreted J3VHH to gp120. Binding to gp120 was significantly higher in supernatant and purified supernatant from engineered *L. rhamnosus* GG comprising *L. rhamnosus* GG SP2 fused to J3VHH compared to negative controls, suggesting that the secreted J3VHH was functional (FIG. 6).

Figure 8:
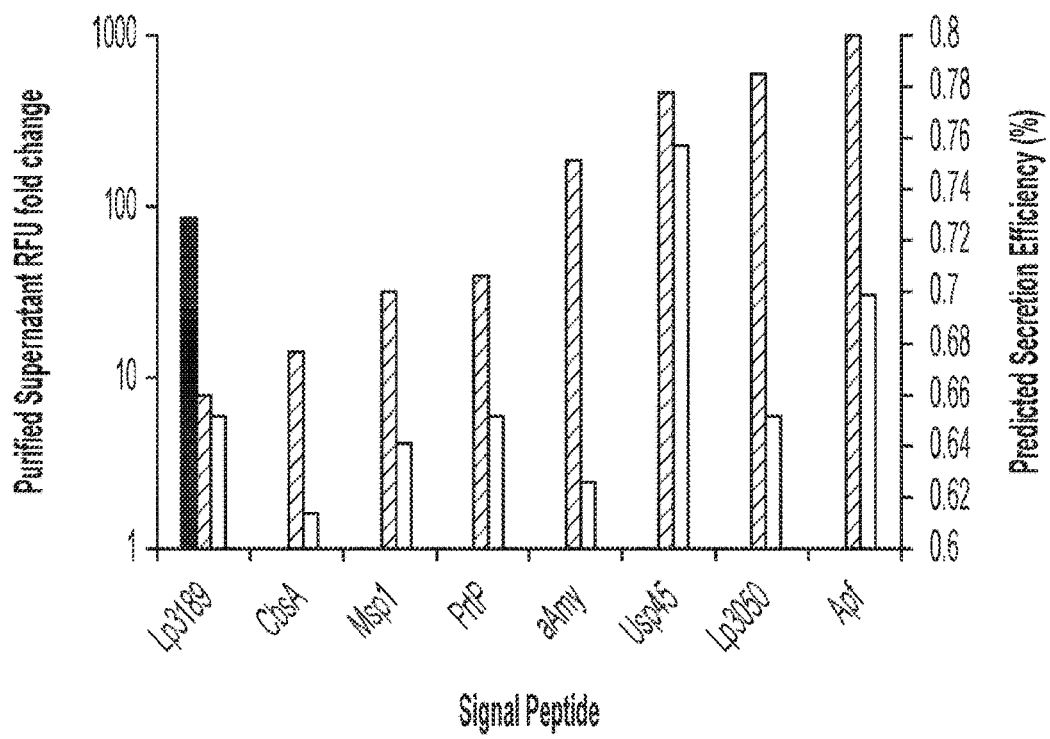
FIG. 8 shows data relating to the predicted secretion efficiency versus the measured secretion efficiency of the indicated naturally occurring secretion signal peptides. Each secretion signal was fused N-terminally to mCherry and tested in *L. gasseri*. mCherry fluorescence in the supernatant was measured as the fold change in relative fluorescence units (RFU). The gray bars indicate the predicted secretion efficiency and the black bars indicate the relative experimentally measured fold change in RFU in *L. gasseri*. The white bars indicate the relative experimentally measured fold change in RFU in *L. rhamnosus* GG.
Figure 9:
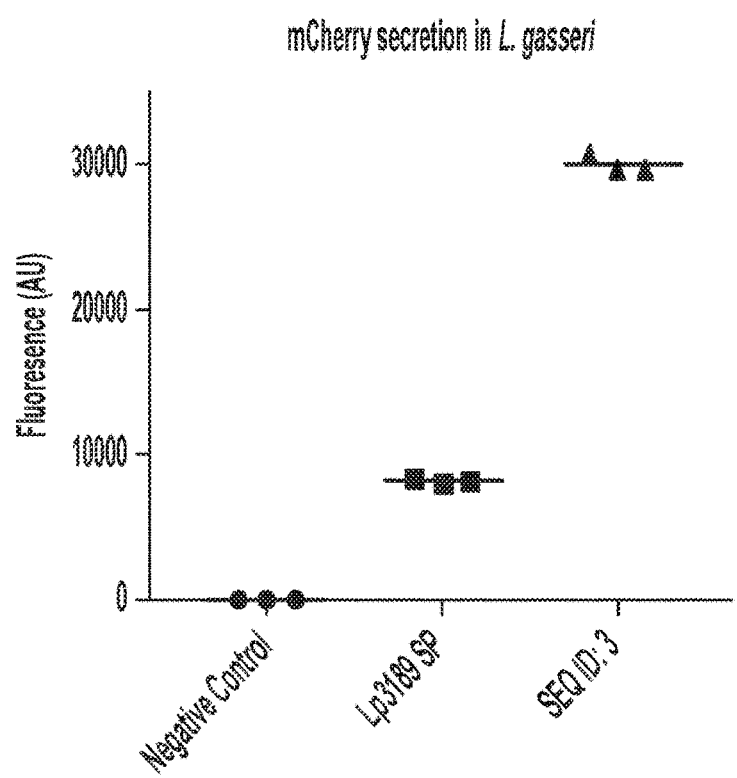
FIG. 9 shows data indicating that the secretion signal peptide with an amino acid sequence provided in SEQ ID NO: 3 (*L. gasseri* SP1) is capable of directing more secretion than the highest performing naturally occurring signal peptide that was tested (Lp3189). Each secretion signal was fused N-terminally to mCherry and tested in *L. gasseri*. The mCherry fluorescence in the supernatant as measured in arbitrary units (AU) is indicated. The fluorescence for the negative control is also shown.

A plot of predicted vs. measured secretion of eight canonical signal peptide sequences reported in the literature was generated (FIG. 8). Each naturally occurring signal peptide was N-terminally fused to the fluorescent protein, mCherry. These constructs were tested in *L. gasseri* to determine the ability of each naturally occurring signal peptide to direct secretion. The level of secretion was measured with the amount of mCherry fluorescence in the purified supernatant. FIG. 8 exhibited the lack of correlation between anticipated secretion efficiency by the existing techniques and actual measured secretion in *L. rhamnosus* GG. A similar result was observed for *L. gasseri*, all but one naturally occurring secretion signal peptide exhibited no measurable secretion (FIG. 8). Secretion was only detected for the secretion signal peptide for Lp3189. Notably, the artificial secretion signal comprising the amino acid sequence provided in SEQ ID NO: 3 (*L. gasseri* SP1) outperformed the secretion signal peptide for Lp3189 (FIG. 9). As in FIG. 8, each secretion signal peptide in FIG. 9 was N-terminally fused to mCherry and the level of secretion was measured with the amount of mCherry fluorescence in the purified supernatant. *L. gasseri* SP1 (SEQ ID NO: 3) secreted more than three times the level of mCherry compared to the secretion signal peptide for Lp3189. Thus, SEQ ID NO: 3 is capable of directing more secretion than the highest performing naturally occurring signal peptide that was tested in *L. gasseri*.

Figure 15:
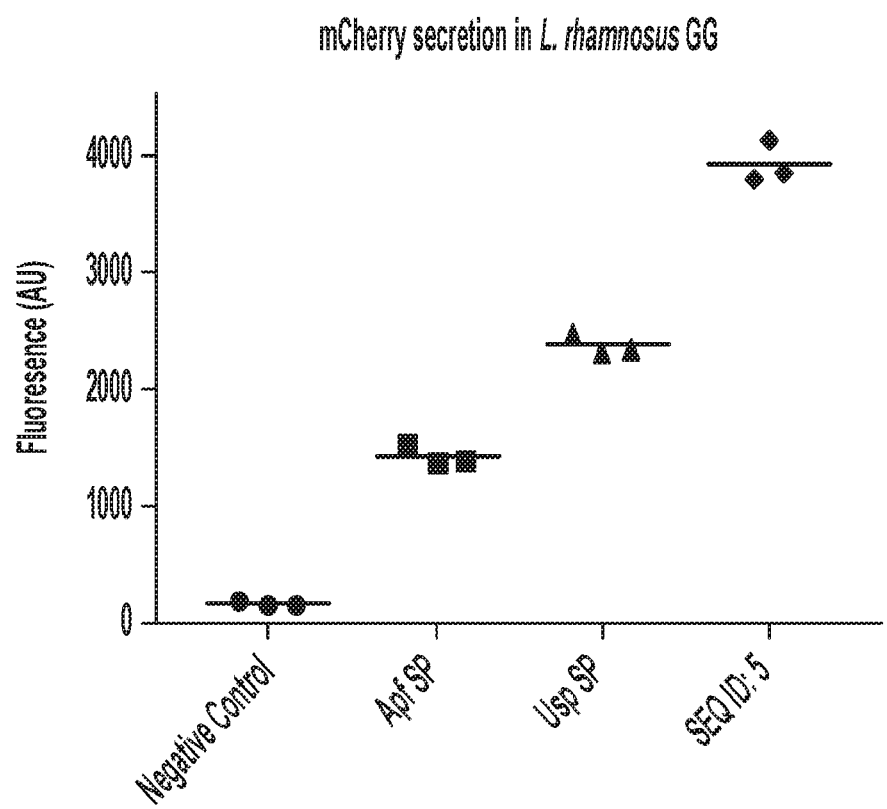
FIG. 15 includes data showing that the secretion signal peptide with an amino acid sequence provided in SEQ ID NO: 5 (*L. rhamnosus* GG SP2) is capable of directing more secretion than the Apf secretion peptide and the Usp secretion peptide. Each secretion signal was fused to mCherry and tested in *L. rhamnosus* GG. The mCherry fluorescence in the supernatant as measured in arbitrary units (AU) is indicated. The fluorescence for the negative control is also shown.
Figure 16:
FIG. 16 is a sequence logo depicting another secretion signal peptide sequence for *L. gasseri* (*L. gasseri* SP2) that is 33 amino acids in length.
Figure 17:
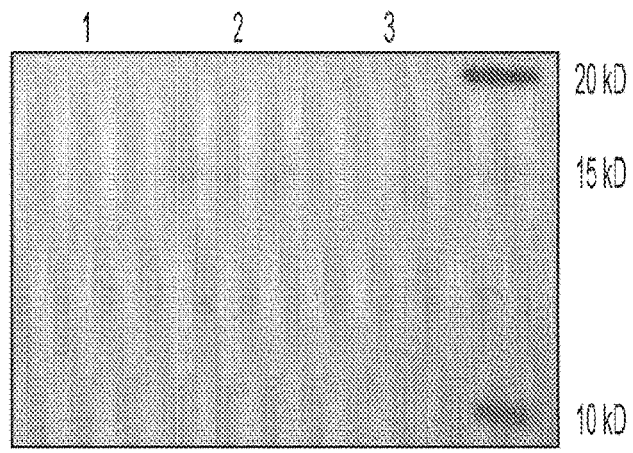
FIG. 17 is a gel image showing that a secretion signal peptide with a sequence provided as SEQ ID NO:7 (*L. gasseri* SP2) is capable of secreting J3-VHH from *L. gasseri*, similar to SEQ ID NO:3 (*L. gasseri* SP1). Lane 1 shows results with a non-binding control, lane 2 shows results with *L. gasseri* SP1-J3-VHH, and lane 3 shows results with *L. gasseri* SP2-J3-VHH.
Figure 18:
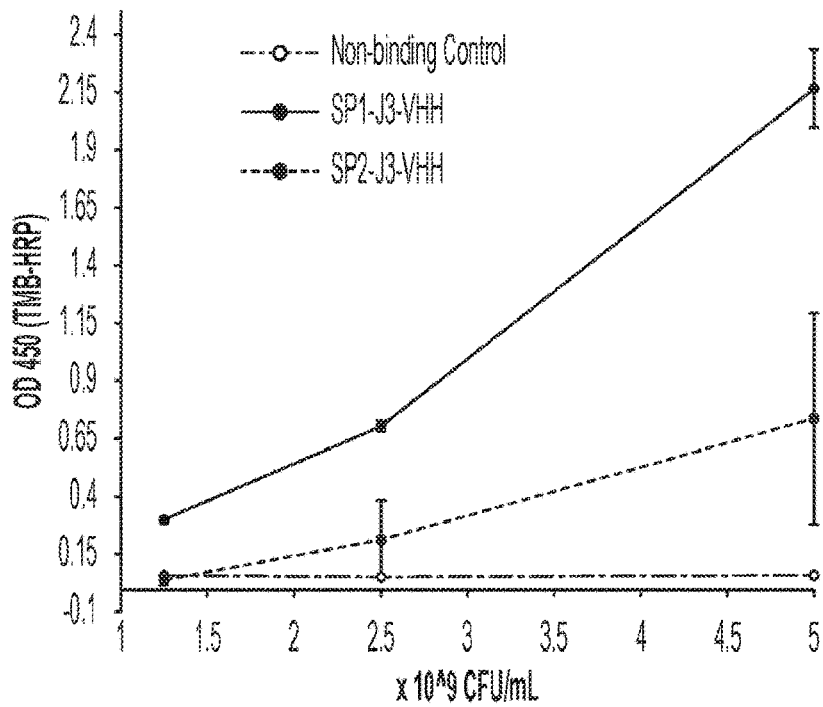
FIG. 18 is a graph indicating that *L. gasseri* SP2 (SEQ ID NO:7) secretes functional J3-VHH from *L. gasseri*. The graph shows the results of an ELISA assay that detects binding to gp120 using an anti-gp120 antibody in unpurified supernatants.
Figure 19A:
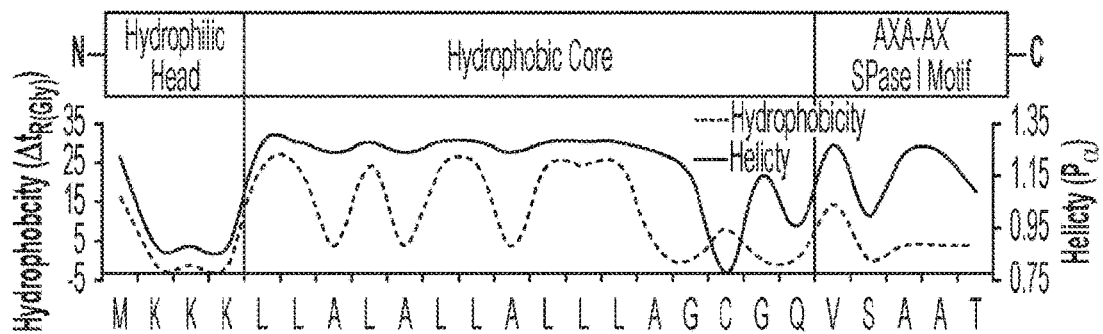
FIGS. 19A-19B are graphs showing two physicochemical amino acid properties (hydrophobicity and helicity) of the motifs present in *L. rhamnosus* GG SP1 (SEQ ID NO:1) (FIG. 19A) and in *L. rhamnosus* GG SP2 (SEQ ID NO:5) (FIG. 19B).
Figure 19B:
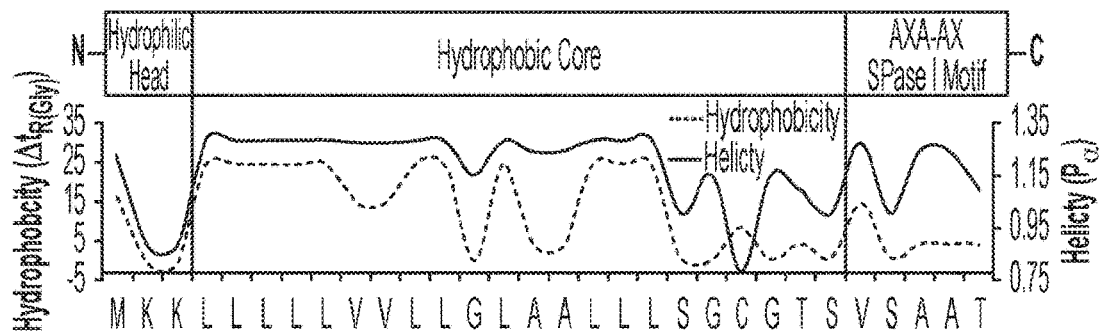
Figure 20A:
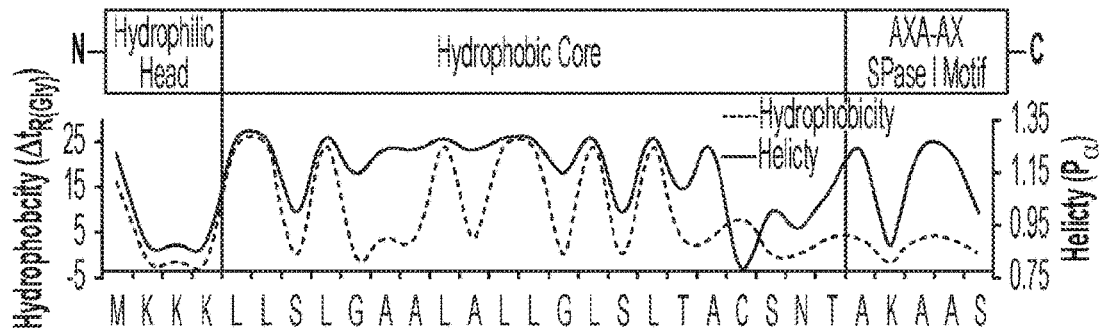
FIGS. 20A-20B are graphs showing two physicochemical amino acid properties (hydrophobicity and helicity) of the motifs present in *L. gasseri* SP1 (SEQ ID NO:3) (FIG. 20A) and in *L. gasseri* SP2 (SEQ ID NO:7) or *L. gasseri* SP3 (FIG. 20B).
Figure 20B:
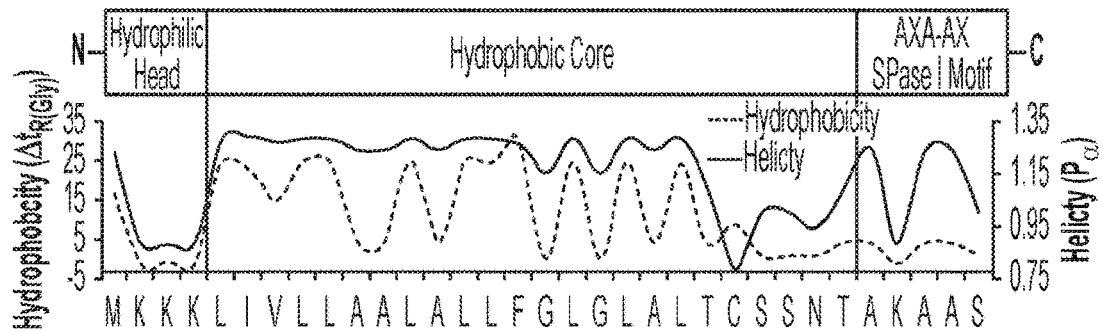

Similarly, the artificial secretion signal comprising the amino acid sequence provided in SEQ ID NO: 5 (*L. rhamnosus* GG SP2 or LGG SP2) outperformed the top two performing secretion signal peptides in LGG shown in FIG. 8 (Apf, Usp). LGG SP2 exhibited secretion levels between 1.5 and 2.75 times higher in purified supernatants than the signal peptides for Usp and Apf, when fused to mCherry (FIG. 15). Of note, the experiment yielding the data for FIG. 9 was performed via purification of 50 mL of bacterial culture, while the data in FIG. 15 was generated with 5 mL of bacterial culture. Therefore, absolute yields between the peptides used in FIG. 9 and FIG. 15 cannot be compared, but a 10× difference would be expected based on the volume of culture used.

Example 2

Therapeutic Applicability of *L. gasseri* SP1 (SEQ ID NO: 3)

Figure 10A:
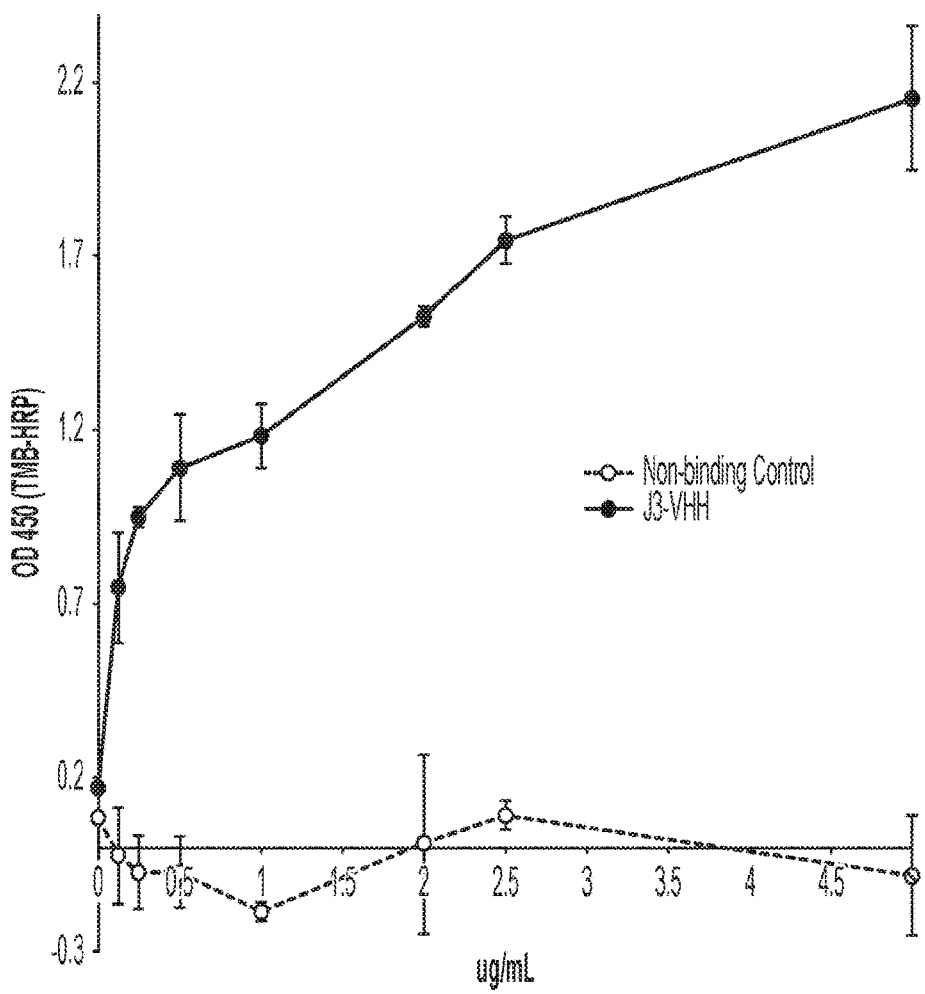
FIG. 10 includes data indicating that the J3VHH secreted by *L. gasseri* SP1 (SEQ ID NO: 3) exhibits comparable HIV neutralization activity to conventionally produced J3VHH as reported in the literature. Panel A shows the results of an ELISA experiment measuring the concentration of J3VHH secreted by *L. gasseri* SP1 on the left axis. Panel B shows 'TZM-b1 data, which assesses HIV neutralization activity. Briefly, this measures the fraction of human, HIV-susceptible cells that are protected by treatment with an antibody. The IC50 of J3VHH secreted by *L. gasseri* SP1 is indicated as the measured IC50. The IC50 of conventionally produced J3VHH as reported in the literature is indicated as the published IC50.
Figure 10B:
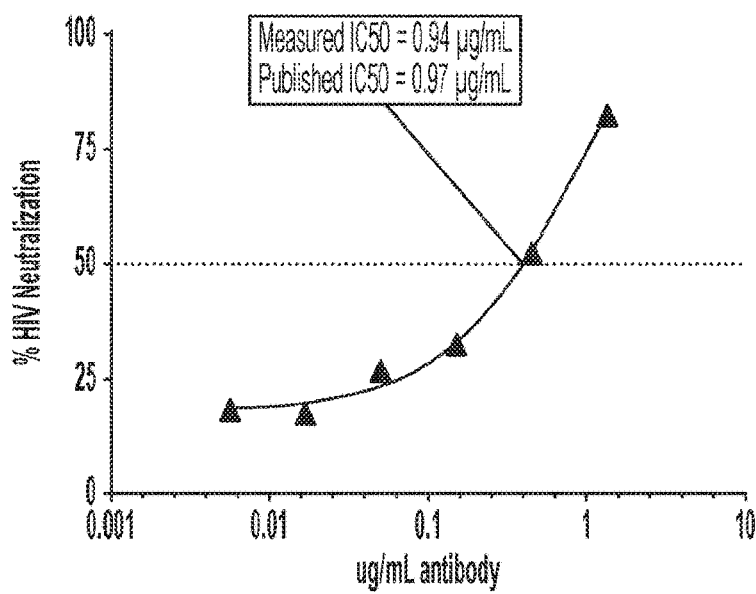

A TZM-bl assay was used to determine whether the anti-HIV antibody fragments (J3VHH) secreted by *L. gasseri* SP1 (SEQ ID NO: 3) were capable of protecting HIV-susceptible cells from HIV infection. Binding of J3VHH was measured (FIG. 10, panel A). The TZM-bl assay was used to measure the fraction of human, HIV-susceptible cells that are protected by treatment with an antibody (FIG. 10, panel B). Notably, J3VHH secreted by *L. gasseri* SP1 exhibits comparable activity (IC50, boxed) to conventionally produced J3VHH as reported in the literature[1]. This demonstrates that proven therapeutic proteins can be produced with essentially equivalent functionality.

Example 3

Figures 12A, 12B:
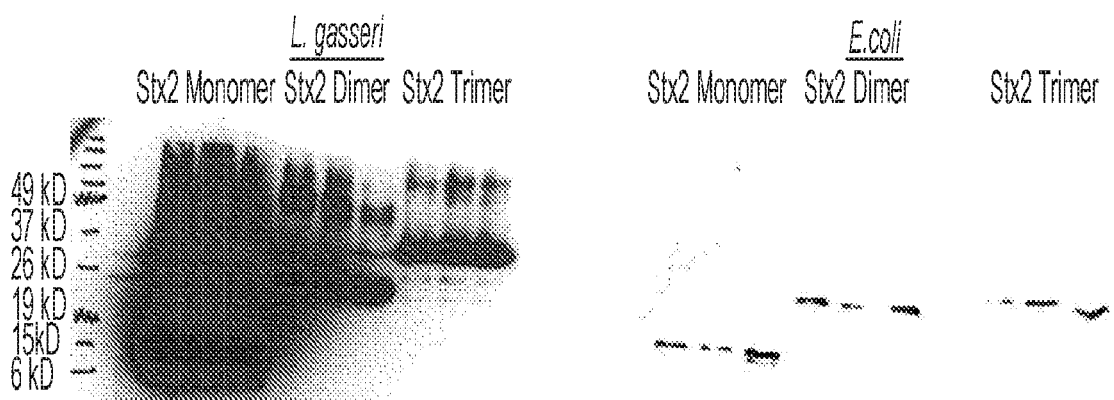
FIGS. 12A-12B show comparative data demonstrating that the engineered *Lactobacilli* (FIG. 12A) can secrete products at greater quantities than *E. coli* (FIG. 12B).
Figure 13A:
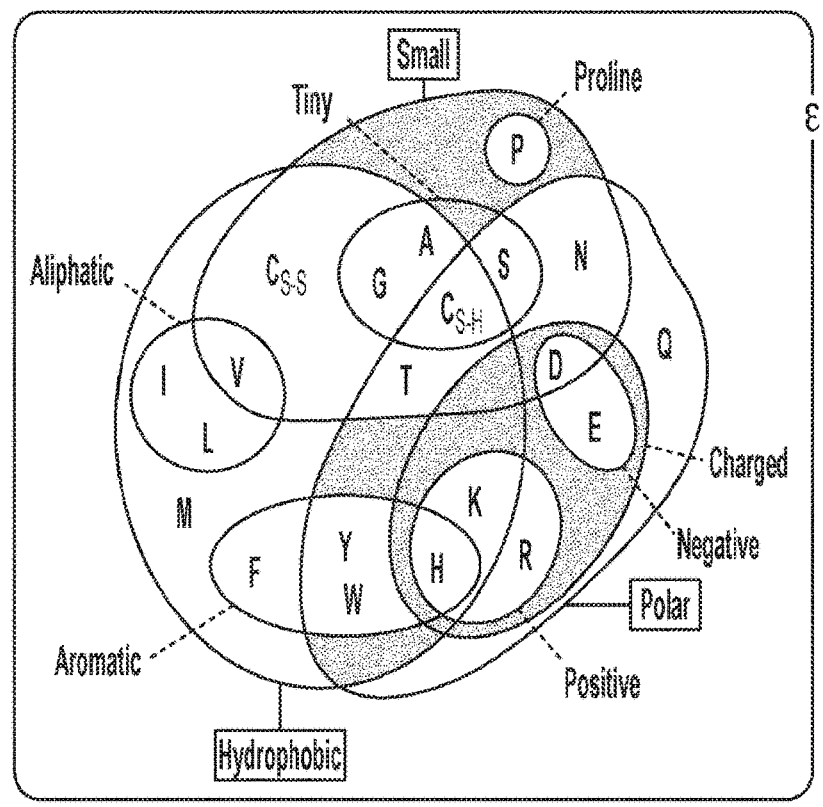
FIG. 13 includes data relating to predictive scoring of SP function by machine learning. Panel A shows a Venn diagram of how certain subsets of amino acids may tolerate substitution with one another in a peptide sequence due to similarities of their physiochemical properties. Panel B shows data relating to linear discriminant analysis of multidimensional functional property data via singular value decomposition (SVD-LDA).
Figure 13B:
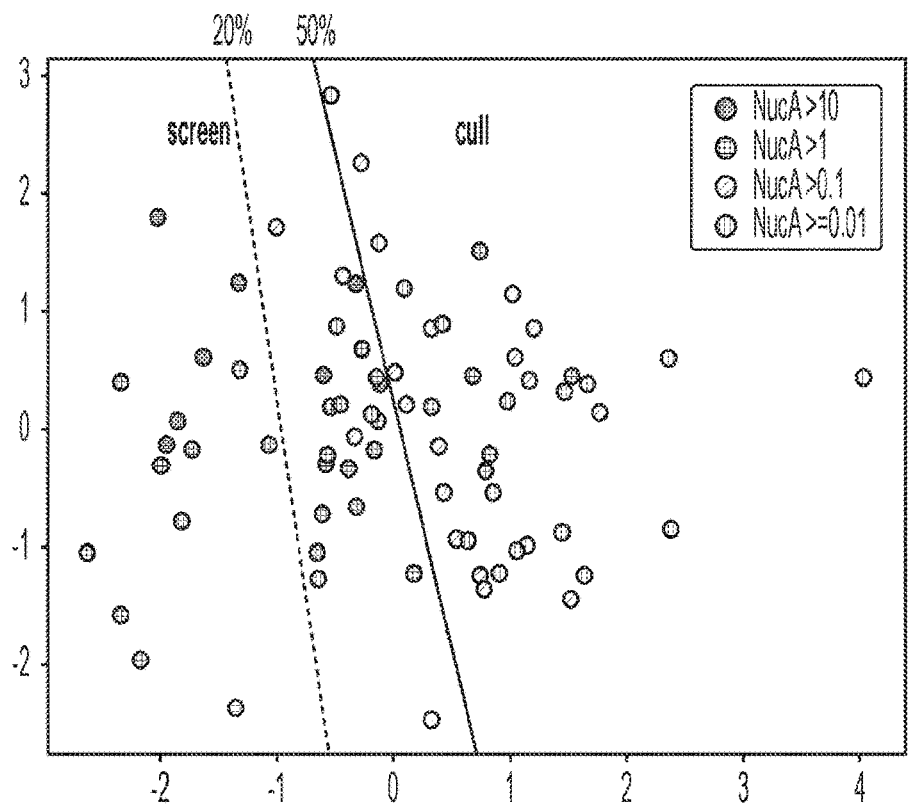
Figure 14:
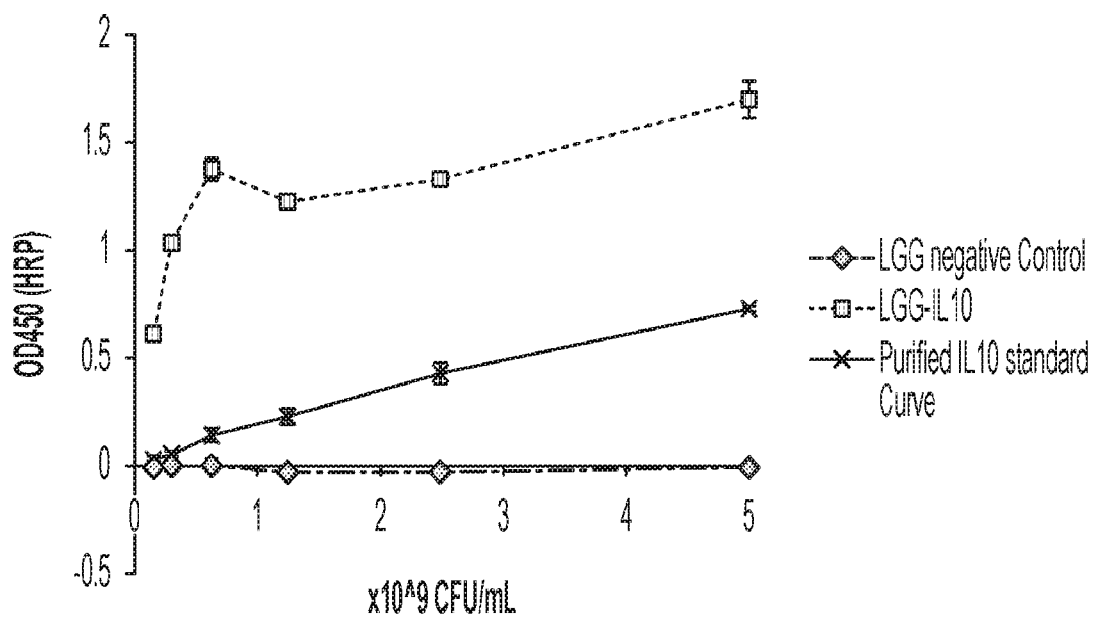
FIG. 14 includes data from an IL-10 capture ELISA with cell-free *L. rhamnosus* GG (LGG) supernatant, compared to a standard curve of purified IL-10. The dilution series is reported as fractions of original culture CFU/mL density; purified IL-10 resuspended in cell-free, negative control culture media.

Impact of Artificial Signal Peptides on Secretion of Anti-Shiga Toxin Antibody Fragments To determine the impact of the artificial signal peptides on secretion of anti-Shiga toxin (Stx2) antibody fragments, *L. gasseri* SP1 (SEQ ID NO: 3) was N-terminally fused to each of three different anti-Shiga toxin antibody fragments and tested in *L. gasseri*. Unpurified supernatant was collected and the secretion of each antibody fragment in unpurified supernatant was detected by western blot with three replicates. The anti-Shiga toxin (Stx2) monomer is a conventional, single domain antibody fragment (17 kDa), and the dimer (33.5 kDa) and trimer (48 kDa) are two and three fused monomers, respectively. Monomers were fused by flexible glycine-serine linkers to produce the dimer and trimer. Each was exposed to an anti-purification staining tag for 20 minutes. As shown in FIG. 12, *L. gasseri* SP1 secreted the Stx2 monomer, Stx2 dimer and the Stx2 trimer (FIG. 12).

Example 4

Predictive Scoring of SP Function by Machine Learning

Provided below is a data analytics method, trained on published data from a heterologous (NucA) secretion library in *L. plantarum*[4], for predicting signal peptide function via analysis of its constituent amino acids. Certain subsets of amino acids may tolerate substitution with one another in a peptide sequence due to similarities of their physicochemical properties (FIG. 13, panel A). Functional properties include C-terminal cleavage motif sequence similarity to computed secretion signal, N-terminal sequence motif length, N-terminal sequence motif hydrophilicity, core sequence length, core sequence hydrophobicity, core sequence transmembrane helix length, core sequence transmembrane helicity and the following ratio: core sequence transmembrane helix length/hydrophobic sequence length. By pairing this with the sequence probabilities given by the position weight matrix generated for the secretion signal peptides, the number of variants in a screen may be reduced, by identifying weak performers in silico. Furthermore, as a machine learning technique, any measured data yielded by a secretion screen of sequences it predicted as strong can be fed back into the model, thus improving the accuracy of its predictions for subsequent screens. An example of linear discriminant analysis of multidimensional functional property data via singular value decomposition is provided in FIG. 13, panel B. The pipeline for predictive scoring of SP function by machine learning comprises the following steps:

1. Using SignalP to generate natural secretion peptides (SP) library of a given strain
2. Using GLAM to generate consensus sequences for given natural SP library;
3. Generating artificial SP library given consensus position width matrix;
4. Predicting artificial SP library member function with SVD-LDA;
5. Filtering out SPs with poor functional likelihood;
6. Performing a functional screen; and
7. If no hits, feedback measured data to step 4 and re-train algorithm, repeat predictions.

Example 5

IL-10 Secretion by LGG

*L. rhamnosus* GG (LGG) was engineered to secrete IL-10 in part to demonstrate that the synthetic secretion signals of the present disclosure function with therapeutic payloads other than a NANOBODY®. The same signal peptide (SEQ ID NO: 1) successfully used previously with Ozoralizumab, Vobariluzumab, anti-HIV NANOBODY®, and fluorescent reporter protein was fused to IL-10. LGG could robustly secrete IL-10 with the same signal peptide, yielding at least 30 μg of cytokine per mL of culture supernatant (FIG. 14). The secretion level reported herein is at least 10× the 3 μg/mL secretion level reported previously (Steidler, L., et al. 2000. *Science* 289 (5483): 1352-55). Unlike *L. lactis*, LGG is not killed by bile salts, which makes it an ideal oral delivery vehicle for therapeutic proteins (e.g., full-length proteins, fusion proteins, peptides, etc.)

Example 6

A Second Functional SP Sequence for *L. gasseri* (*L. gasseri* SP2, SEQ ID NO:7)

Another synthetic SP was tested based on a second consensus sequence for *L. gasseri* (SP2), where GLAM2 was preset to the average length of all natural, *L. gasseri* signal peptides: 33aa (FIG. 16).

*L. gasseri* SP2 was validated via protein gel analysis of purified supernatant from recombinant *L. gasseri* expressing J3-VHH fused to *L. gasseri* SP2 and compared to *L. gasseri* SP1 (SEQ ID NO:3, length=30aa). *L. gasseri* SP2 secreted a comparable (though slightly less) amount of protein compared to *L. gasseri* SP1 (expected size 14.3 kD) (FIG. 17). The gel result also indicates there is no detectable amount of un-cleaved protein, indicating both synthetic SPs are efficiently processed by Signal Peptidase I.

The secreted product was validated to be functional, as shown by an anti-gp120 ELISA with unpurified supernatants (FIG. 18). The binding strength per CFU indicated by this assay is also consistent with the lower amount of protein seen visually by gel for *L. gasseri* SP1 compared to *L. gasseri* SP2—indicating that shorter synthetic SP lengths may be generally desirable.

Example 7

Analysis of Pertinent Physicochemical Characteristics of Permitted Amino Acid Substitutions for Given Consensus At least two synthetic signal peptide sequences have been shown herein to functionally secrete heterologous proteins in *L. rhamnosus* GG and *L. gasseri*. Within each example, entirely different signal peptides were generated based on a distinct consensus sequences—one based on the average signal peptide length for the given species (SP2), and one where the GLAM2 consensus software was set to randomly sample different lengths and predict the optimal length for itself (SP1). To compare these two sequences, two physicochemical amino acid properties (hydrophobicity and helicity) were plotted vis-à-vis each SP's motifs (the N-terminal hydrophilic head sequence, the hydrophobic core sequence, and the C-terminal Type I Signal Peptidase cleavage site). FIG. 19A shows the hydrophobicity and helicity curves for *L. rhamnosus* GG SP1 (SEQ ID NO: 1) and FIG. 19B shows the hydrophobicity and helicity curves for *L. rhamnosus* GG SP2 (SEQ ID NO: 5). FIG. 20A shows the hydrophobicity and helicity curves for *L. gasseri* SP1 (SEQ ID NO: 3) and FIG. 20B shows the hydrophobicity and helicity curves for *L. gasseri* SP2 (SEQ ID NO: 7).

The consensus for the Hydrophilic N-terminal Head sequence and the Type I Signal Peptidase cleavage site were essentially the same between SP1 and SP2 for each strain, with two exceptions: (1) for *L. rhamnosus* GG, the N-terminal sequence was one K shorter in SP1 vs. SP2, which is likely a proportional difference with overall length; (2) for *L. gasseri* the last amino acid of the cleavage site was a S in SP1 and a T in SP2, however these amino acids are close cognates (corresponding to conservative amino acid substitution group e described above), and the final position is understood to be more variable in this motif (i.e., AXA-AX).

They differed in the content of their hydrophobic cores, but only by near-relative amino acid substitutions—within I, L, & V (corresponding to conservative amino acid substitution group a described above), and A & G (corresponding to conservative amino acid substitution group d described above)—resulting in similar hydrophobicity and helicity profiles curves despite the reduction in length—interestingly, to the previously characterized decline in sequence hydrophobicity and helicity that begins 5-6 amino acids prior to the cleavage motif is conserved, despite the reduction in the overall length. This indicates a putative importance to this feature for signal peptide processing, which has not been discussed in published literature to date. Amino acid substitutions that preserve these hydrophobicity and helicity curves are thus likelier to yield functional SP variants.

Example 8

Secretion of IL10 by *L. rhamnosus* GG In Vivo

Figure 21:
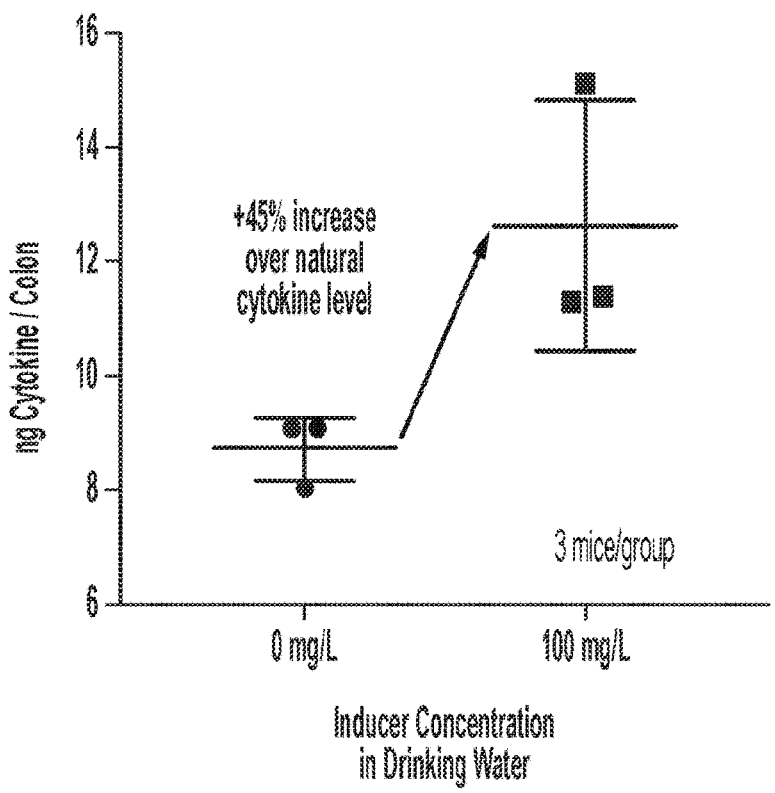
FIG. 21 is a graph showing in vivo delivery of IL10 by recombinant *L. rhamnosus* GG.

A proof of concept experiment was performed to demonstrate that *Lactobacillus* engineered with synthetic signal peptides exhibit comparable function in vivo as in vitro. In this instance, healthy mice (strain balb/c) were inoculated with 10^10 CFUs of recombinant *L. rhamnosus* GG engineered to secrete IL10 (using LGG SP2, SEQ ID NO: 5), once a day for 5 consecutive days via oral gavage. During this period, one group of mice was fed drinking water that included 0.1 mg/mL of anhydrotetracycline—which induces the expression of SP2-IL10, controlled by a switchable promoter sensitive to anhydrotetracycline. Another group was not provided any inducer, and was used as a negative control. On the fifth day, mice were sacrificed and whole colon tissue was harvested, homogenized, and measured IL10 secretion yields exactly as done previously with culture supernatants—an IL10 capture ELISA with a standard curve of purified IL10. As IL10 is naturally expressed in healthy colon tissue, there is background signal in the negative control where no inducer is provided. However, induction increases the level of colonic IL10 by 45%, and results in a 3.9 ng of delivered IL10 to whole colon by induced recombinants (FIG. 21).

Previous work showed that 0.28 ng of IL10 delivered to whole colon by recombinant IL10 secreting *L. lactis* provided to mice 17 times a day conferred a 30% reduction of colitis symptoms in a DSS-colitis model [5]. Surprisingly, the recombinant *L. rhamnosus* GG used herein, provided to mice only once a day, delivers 3.9 ng of IL10—thus, ~14 times more IL10 was delivered in a fraction of the time, and required a much lower dose of bacteria, relative to previous methods.

Example 9

Secretion of GLP1 by *L. rhamnosus* GG In Vitro

Figure 22:
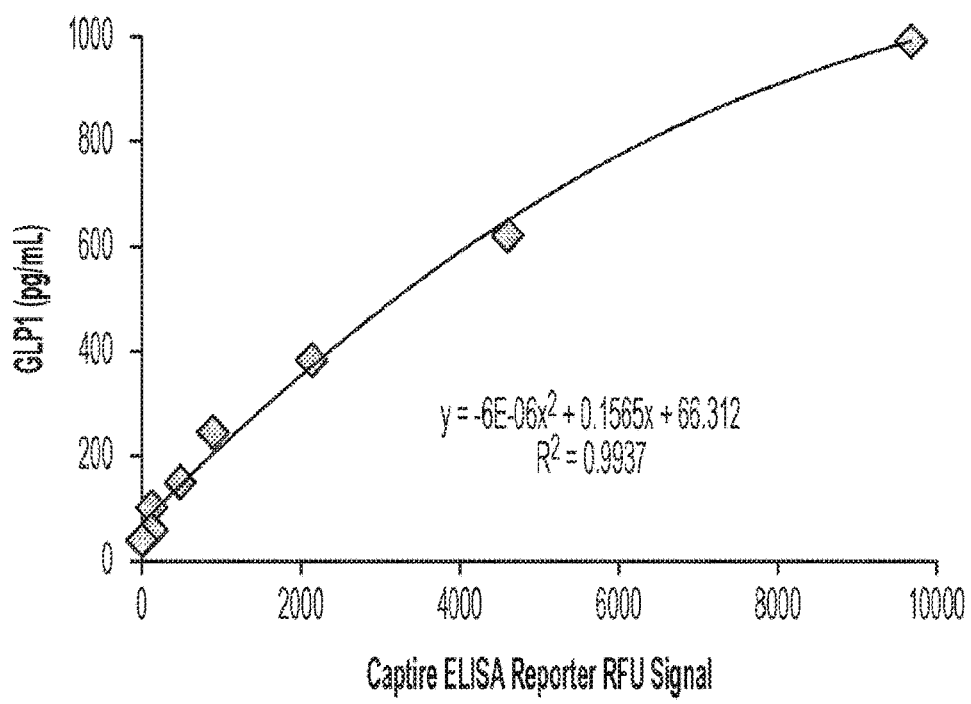
FIG. 22 is a graph showing a vendor purified GLP2 standard capture ELISA concentration curve fit.
Figure 23:
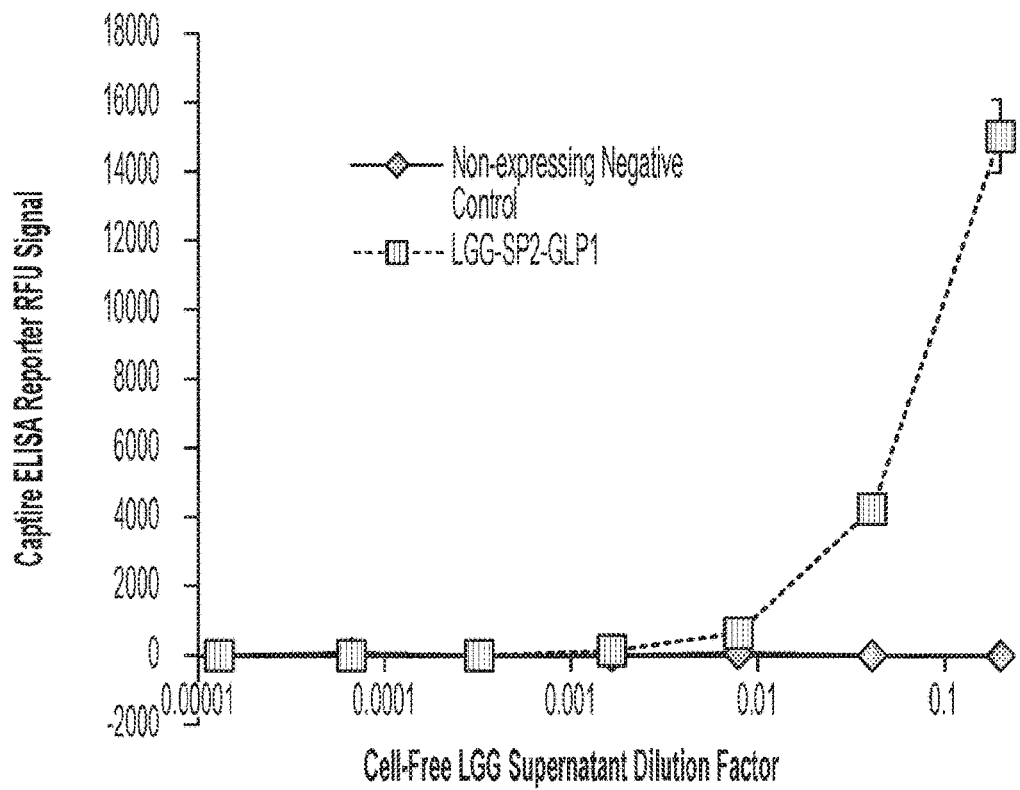
FIG. 23 is a graph showing in vitro secretion of GLP1 by recombinant *L. rhamnosus* GG.

Glucagon-like peptide 1 (GLP1) is a endocrine hormone naturally produced by colonic L-cells, that stimulates insulin production and thus improves glucose tolerance. It also contributes to a sense of satiation upon eating, and has been observed to influence lipid metabolism, reverse endothelial dysfunction, and reduce atrial blood pressure. As such, it has been proposed as a therapeutic candidate for diabetes, obesity, and cardiovascular disease [6]. However, GLP1 is rapidly degraded into an inactive form in the blood stream and is digested when administered orally. Thus, engineered microbes offer a unique opportunity for GLP1 delivery in a manner that is analogous to native GLP1 expression, which occurs in the colon. As demonstrated here, the synthetic signal peptides of the present disclosure facilitate secretion of GLP1, thus indicating that hormones composed of small peptides (2-5 kDa) are an additional payload class accessible to secretion by the methods provided herein. The gut symbiont *L. rhamnosus* GG (SEQ ID NO: 5) was engineered to secrete GLP1 under induction using SP2. Secreted GLP1 was measured in cell-free supernatant after 4 hours of induction by anhydrotetracycline in vitro using a GLP1 capture ELISA assay with a purified GLP1 standard. Surprisingly, this recombinant strain can secrete and deliver up to 5.3 ng/mL of GLP1 (see FIGS. 22 and 23).

Example 10

Secretion of hBD1 by *L. gasseri*

Figure 24:
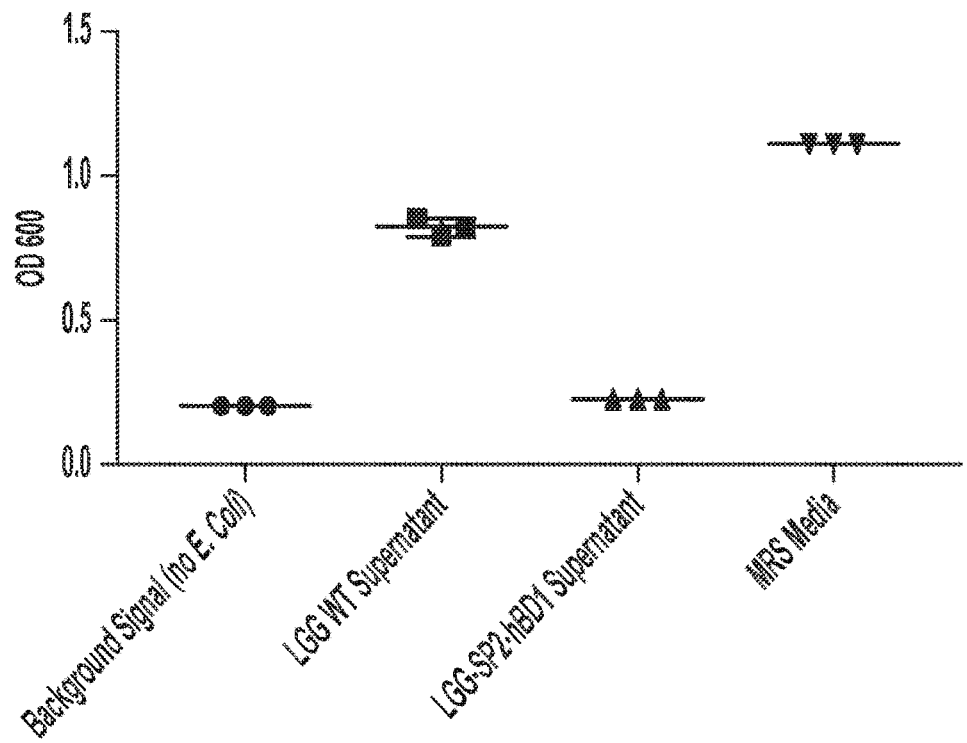
FIG. 24 is a graph showing *E. coli* ATCC 25922 growth inhibition by hBD1 secreted by *L. gasseri*.

Another protein payload class for secretion by synthetic signal peptides are small peptide effectors ranging from 10-50 amino acids in length—including antimicrobial peptides and defensins. One exemplary instance of this class of peptides is human beta defensin 1 (hBD1). This peptide is an ideal payload for this application as it is non-toxic to *Lactobacilli* [7] while having anti-bacterial activity via direct microbicidal activity and chemotactically driven effector immune cell recruitment [8]. Applications for hBD1 secreted by human microbiota can be applied for the treatment of any gram-positive infection in any mucosal site to which such bacteria can be delivered. This experiment tested whether supernatant from induced recombinant *L. gasseri* engineered to secrete hBD1 using SP1 can inhibit growth of the pathogenic strain *E. coli* ATCC 25922. It is known that hBD1 exhibit a minimum inhibitory concentration of this strain between 5-10 µg/mL [8]. Cell-free supernatant from *L. gasseri* cultures induced for 6 hours was mixed with *E. coli* cultures pre-grown to early exponential phase (OD values ranging from 0.25 to 0.35) at a 50:50 ratio. Growth of *E. coli* permitted by unmodified *L. gasseri*, hBD1-secreting *L. gasseri*, and *Lactobacillus* growth medium (MRS) was measured in triplicate and compared against background optical density signals (in MRS with no *E. coli*) after 20 hours in 37° C. Surprisingly, while WT *L. gasseri* inhibited growth bacteriostatically by roughly 32%, likely via naturally secreted bacteriocins, hBD1 secreting *L. gasseri* prevented *E. coli* growth by 98% (FIG. 24).

Materials and Methods

Growth Conditions

*Lactobacilli* were cultured with MRS media in 37 degrees Celsius or room temperature under erythromycin selection when growing transformed cultures. Anhydrous Tetracycline was added at concentrations anywhere up to 500 ng/mL when growing cells for the purposes of producing protein. Typically, cells were grown conventionally until mid-log growth phase (optical density=0.4-0.6) and then Anhydrous Tetracycline was added until stationary phase is reached (OD=1-1.2). The second phase of growth can take place in a few hours in 37 degrees Celsius or overnight at room temperature. *L. gasseri* was grown in a shaking, aerated incubator. *L. rhamnosus* GG was grown in anaerobic conditions.

Reagents
1.

| MRS media: Mix 55 g of cocktail below with 1 L distilled water, Autoclave 15 min Difco ™ Lactobacilli MRS Agar Approximate Formula* Per Liter | |
|---|---|
| Proteose Peptone No. 3 | 10.0 g |
| Beef Extract | 10.0 g |
| Yeast Extract | 5.0 g |
| Dextrose | 20.0 g |
| Polysorbate 80 | 1.0 g |
| Ammonium Citrate | 2.0 g |
| Sodium Acetate | 5.0 g |
| Magnesium Sulfate | 0.1 g |
| Manganese Sulfate | 0.05 g |
| Dipotassium Phosphate | 2.0 g |

Ensure that the media has not caramelized by checking for brown syrup at the bottom of the bottle 2. MRS agar: MRS media formulation+1.5% w/v of BactoAgar, Autoclave 15 min 3. Glycine stock solution: Mix 20 g of glycine with 100 mL distilled water, filter sterilize with a 0.22 µM membrane.

4. Electroporation Conditioner 1: 0.5 M sucrose, 7 mM potassium phosphate, 1 mM magnesium chloride solution in distilled water; filter sterilize with a 0.22 µM membrane.

5. Electroporation Conditioner 2: 925 mM sucrose, 3.5 mM magnesium chloride solution in distilled water; filter sterilize with a 0.22 µM membrane.

6. Recovery Media 1: Supplement an aliquot of MRS media with 20 mM magnesium chloride, 2 mM calcium chloride; filter sterilize with a 0.22 µM membrane.

7. Recovery Media 2: Supplement an aliquot of MRS media with 0.5 M sucrose, 0.1 M magnesium chloride; filter sterilize with a 0.22 µM membrane.

8. STE media: 6.7% saccharose, 50 mM Tris-Cl pH 8, 1 mM EDTA; filter sterilize with a 0.22 µM membrane.

Methods to Introduce Constructs into *Lactobacilli*

1. Inoculate pre-culture of Lactobacillus in MRS media, 1 mL per transformation required 2. Grow overnight or to density (optical density of 1.0 or more) as per the requirements of the strain, e.g.:
    a. *L. rhamnosus* GG: 37 degrees in an anaerobic jar with 2.5 g palladium catalyst supplemented with BD GASPAK™ rated for anaerobic culture (Ref #260683)
    b. *L. gasseri:* 37 degrees, aerobic conditions 3. Subculture pre-cultures at 1/10 dilution in MRS media supplemented with Glycine stock solution to a final concentration of 0.25-2.5% (optimized on a strain by strain basis)
    a. *L. rhamnosus* GG: 2% glycine
    b. *L. gasseri:* 0.5% glycine 4. Incubate to an optical density of 0.25

5. Pause incubation and supplement media with 0-20 µg of ampicillin
    a. *L. rhamnosus* GG: 10 µg
    b. *L. gasseri:* 0 µg 6. Incubate to an optical density of 0.5

7. Pellet cells by centrifugation at 2000-6000 G for 15 min, in 4-21 degrees ambient temperature
    a. *L. rhamnosus* GG: 5000 G, 21 degrees
    b. *L. gasseri:* 3500 G, 4 degrees 8. Mechanically resuspend cells with 0.5 volume of Electroporation Conditioner and mix briefly (choice of Conditioner to be optimized on a strain by strain basis)
    a. *L. rhamnosus* GG: Electroporation Conditioner 1
    b. *L. gasseri:* Electroporation Conditioner 2

9. Pellet cells as per step 7

10. Repeat wash as per step 8

11. Pellet cells as per step 7

12. Mechanically resuspend cells with 100 uL of Electroporation Conditioner per 10 mL of original MRS+glycine culture volume 13. Aliquot 100 uL of resuspended cells into a 0.2 cm electroporation cuvette, pre-chilled on ice 14. Mix 1-5 uL of plasmid DNA with 50-500 ng of DNA dissolved in TE buffer (input DNA amount optimized on a strain by strain basis)
    a. *L. rhamnosus* GG: 100-200 ng DNA
    b. *L. gasseri:* 400 ng DNA 15. Electroporate with following conditions depending on Electroporation Conditioner used
    a. Electroporation Conditioner 1—Peak voltage: 1.7 kV, capacitance: 25 uF, parallel resistance: 200 ohm
    b. Electroporation Conditioner 2—Peak voltage: 1.5 kV, capacitance: 25 uF, parallel resistance: 800 ohm 16. Resuspend electroporated cells in following conditions depending on Electroporation Conditioner used
    a. Electroporation Conditioner 1—3 mL Recovery Media 1
    b. Electroporation Conditioner 2—1 mL Recovery Media 2

17. Recover the cells via incubation as per the cells growth conditions, for 2-4 hours
    a. *L. rhamnosus* GG: 3 hours
    b. *L. gasseri:* 2 hours 18. Spread 100 uL of the recovered cells (or concentrate/dilution thereof) on MRS agar supplemented with the appropriate antibiotic concentration for the plasmid's selection marker, e.g.:
    a. *L. rhamnosus* GG: 10 µg/mL erythromycin
    b. *L. gasseri:* 4 µg/mL erythromycin 19. Incubate 48-72 hours in the same growth conditions as used for liquid culture for selected strain
    a. *L. rhamnosus* GG: 37 degrees in an anaerobic jar with 2.5 g palladium catalyst supplemented with BD GASPAK™ rated for anaerobic culture (Ref #260683) for 48 hours
    b. *L. gasseri:* 37 degrees, aerobic conditions for 72 hours 20. For DNA diagnostics following transformation
    a. *L. rhamnosus* GG: Pick 1 uL of colony biomass and resuspend for lysis in 16 uL STE buffer (pH 8)+1.6 uL Lysozyme+2 uL Proteinase K+0.4 uL Mutanolysin. Incubate 30 mins at 37 degrees. Use 0.5-1 uL of lysed material as template in a PCR reaction, or use entire volume for RCA based Sanger sequencing as necessary.
    b. *L. gasseri*: Pick entire colony biomass and resuspend in 3 mL MRS media supplemented with selective antibiotic and grow 24-48 hours until optical density 1.0. Use 0.5-1 uL of culture directly as template in a PCR reaction, or extract whole plasmid DNA from liquid as per standard techniques (e.g. Qiagen® Miniprep)
    c.

Method to Compute Artificial Secretion Sequences

1) SignalP was used to computationally mine all possible, natural SP sequences from the proteome (sourced from NCBI proteome database) of a given strain we wish to engineer secretion for (i.e. *L. rhamnosus* proteome for *L. rhamnosus* SP 1 and *L. rhamnosus* SP 2, *L. gasseri* proteome for *L. gasseri* SP).

2) An amino acid fasta file of the natural SP sequences was generated, and put into GLAM, with the desired length of the consensus sequence (a length of 25 was used for *L. rhamnosus* SP 1, 30 for *L. rhamnosus* SP2, 30 for *L. gasseri*

SP1). Usually, the average length of the natural SP pool generated in step 1 was used.

3) GLAM generates a position weight matrix for the possible consensus sequences given the FASTA file and desired length—the most likely consensus sequence. The highest probability amino acid for each given sequence position was taken and used as artificial SP sequences—exhibited by the top most letters in the sequence logo images in FIG. 1.

Sequences

```
L. rhamnosus GG SP1
                                            (SEQ ID NO: 1)
MKKKLLALALLALLLAGCGQVSAAT L. rhamnosus GG SP1 nucleic acid
                                            (SEQ ID NO: 2)
ATGAAGAAGAAATTGTTGGCATTGGCATTGTTGGCATTGTTGTTGGC

AGGCTGCGGCCAAGTTTCAGCAGCAACC

L. gasseri SP1
                                            (SEQ ID NO: 3)
MKKKLLSLGAALALLGLSLTACSNTAKAAS L. gasseri SP1 nucleic acid
                                            (SEQ ID NO: 4)
ATGAAAAAAAATTATTATCATTAGGTGCTGCTTTAGCTTTATTAGG

TTTATCATTAACTGCTTGTTCAAATACTGCTAAAGCTGCTTCA

L. rhamnosus GG SP2
                                            (SEQ ID NO: 5)
MKKLLLLLVVLLGLAALLLSGCGTSVSAAT L. rhamnosus GG SP2 nucleic acid
                                            (SEQ ID NO: 6)
ATGAAAAAATTGTTGTTGTTGTTGGTTGTTTTGTTGGGCTTGGCAGC

ATTGTTGTTGTCAGGCTGCGGCACCTCAGTTTCAGCAGCAACC

L. gasseri SP2
                                            (SEQ ID NO: 7)
MKKKLIVLLAALALLFGLGLALTCSSNTAKAAS L. gasseri SP2 nucleic acid
                                            (SEQ ID NO: 8)
ATGAAAAAAAAATTGATTGTTTTGTTGGCAGCATTGGCATTGTTGTT

TGGCTTGGGCTTGGCATTGACCTGCTCATCAAATACCGCAAAAGCAG

CAACC

GLP1:
                                            (SEQ ID NO: 9)
HDEFERHAEGTFTSDVSSYLEGQAAKEFIAWLVKGRG

HBD1:
                                            (SEQ ID NO: 10)
GNFLTGLGHRSDHYNCISSGGQCLYSACPIFTKIQGTCYRGKAKCCK

L. gasseri SP3
                                            (SEQ ID NO: 11)
MKKKLIVLLAALALLFGLGLALTCSSNTAKAAT
```

REFERENCES

1. McCoy, L. E. et al. *J. Exp. Med.* 209, 1091-1103 (2012).
2. Matz, J. et al. *J. Virol.* 87, 1137-1149 (2013).
3. Mata-Fink, J. et al. *J. Mol. Biol.* 425, 444-456 (2013).
4. Mathiesen, G. et al. *BMC Genomics* 10, 425 (2009).
5. Steidler et al. *Science* 2000
6. Ryan et al. *Nature Scientific Reports* 2017
7. Lebeer, S. et al. *Microbiology Biotechnology* 4(3) (2010)
8. Wu Z. et al. *PNAS* 100(15), 8880-8885 (2003)

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean ±10% of the recited numerical value.

Where a range of values is provided, each value between the upper and lower ends of the range are specifically contemplated and described herein.

What is claimed is:

1. An artificial signal peptide comprising an amino acid sequence that has at least 95% sequence identity to an amino acid sequence of any one of SEQ ID NO: 1, SEQ ID NO: 3, SEQ ID NO: 5, SEQ ID NO: 11, and SEQ ID NO: 7.

2. The artificial signal peptide of claim 1, wherein the amino acid sequence has at least 98% sequence identity to an amino acid sequence of any one of SEQ ID NO: 1, SEQ ID NO: 3, SEQ ID NO: 5, SEQ ID NO: 11, and SEQ ID NO: 7.

3. The artificial secretion signal peptide of claim 2, wherein the amino acid sequence comprises the amino acid sequence of any one of SEQ ID NO:1, SEQ ID NO:3, SEQ ID NO:5, SEQ ID NO: 11, and SEQ ID NO:7.

4. A protein fused to the artificial secretion signal peptide of claim 1.

5. The protein of claim 4, wherein the artificial secretion signal peptide is fused to the N-terminus of the protein.

6. The protein of claim 4, wherein the protein is a therapeutic protein.

7. The protein of claim 6, wherein the protein is an antibody, optionally wherein the antibody binds specifically to a viral antigen or a microbial antigen.

8. The protein of claim 6, wherein the therapeutic protein is a cytokine, optionally wherein the cytokine is IL-10.

9. The protein of claim 6, wherein the therapeutic protein is an endocrine hormone, optionally wherein the endocrine hormone is glucagon-like peptide 1 (GLP1).

10. The protein of claim 6, wherein the therapeutic protein is an antimicrobial peptide, optionally wherein the antimicrobial peptide is human beta defensin 1 (hB D1).

11. The artificial secretion signal peptide of claim 1 comprising the amino acid sequence of SEQ ID NO:5, wherein the artificial secretion signal peptide is fused to a therapeutic protein.

12. The artificial secretion signal peptide of claim 11, wherein the therapeutic protein is selected from interleukin-10 (IL-10), glucagon-like peptide 1 (GLP1), and human beta defensin 1 (hBD1).

* * * * *

SEQUENCE LISTING

```
<160> NUMBER OF SEQ ID NOS: 11

<210> SEQ ID NO 1
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 1

Met Lys Lys Lys Leu Leu Ala Leu Ala Leu Leu Ala Leu Leu Leu Ala
1               5                   10                  15

Gly Cys Gly Gln Val Ser Ala Ala Thr
            20                  25
```

<210> SEQ ID NO 2
<211> LENGTH: 75
<212> TYPE: DNA
<213> ORGANISM: Artificial Sequence
<220> FEATURE:
<223> OTHER INFORMATION: Synthetic Polynucleotide

<400> SEQUENCE: 2
atgaagaaga aattgttggc attggcattg ttggcattgt tgttggcagg ctgcggccaa    60
gtttcagcag caacc                                                    75

<210> SEQ ID NO 3
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 3

Met Lys Lys Lys Leu Leu Ser Leu Gly Ala Ala Leu Ala Leu Leu Gly
1               5                   10                  15

Leu Ser Leu Thr Ala Cys Ser Asn Thr Ala Lys Ala Ala Ser
            20                  25                  30

<210> SEQ ID NO 4
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 4
atgaaaaaaa aattattatc attaggtgct gctttagctt tattaggttt atcattaact    60
gcttgttcaa atactgctaa agctgcttca                                    90

<210> SEQ ID NO 5
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 5

Met Lys Lys Leu Leu Leu Leu Val Val Leu Leu Gly Leu Ala Ala
1               5                   10                  15

Leu Leu Leu Ser Gly Cys Gly Thr Ser Val Ser Ala Ala Thr
            20                  25                  30

<210> SEQ ID NO 6
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 6
atgaaaaaat tgttgttgtt gttggttgtt ttgttgggct tggcagcatt gttgttgtca    60
ggctgcggca cctcagtttc agcagcaacc                                    90

<210> SEQ ID NO 7
<211> LENGTH: 33
<212> TYPE: PRT

<213> ORGANISM: Artificial Sequence
<220> FEATURE:
<223> OTHER INFORMATION: Synthetic Polypeptide

<400> SEQUENCE: 7

Met Lys Lys Lys Leu Ile Val Leu Leu Ala Ala Leu Ala Leu Leu Phe
1               5                   10                  15

Gly Leu Gly Leu Ala Leu Thr Cys Ser Ser Asn Thr Ala Lys Ala Ala
            20                  25                  30

Ser

<210> SEQ ID NO 8
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 8
atgaaaaaaa aattgattgt tttgttggca gcattggcat tgttgtttgg cttgggcttg      60
gcattgacct gctcatcaaa taccgcaaaa gcagcaacc                            99

<210> SEQ ID NO 9
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 9

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 10
<211> LENGTH: 47
<212> TYPE: PRT
<213> ORGANISM: Artificial Sequence
<220> FEATURE:
<223> OTHER INFORMATION: Synthetic Polypeptide

<400> SEQUENCE: 10

Gly Asn Phe Leu Thr Gly Leu Gly His Arg Ser Asp His Tyr Asn Cys
1               5                   10                  15

Ile Ser Ser Gly Gly Gln Cys Leu Tyr Ser Ala Cys Pro Ile Phe Thr
            20                  25                  30

Lys Ile Gln Gly Thr Cys Tyr Arg Gly Lys Ala Lys Cys Cys Lys
        35                  40                  45

<210> SEQ ID NO 11
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 11

Met Lys Lys Lys Leu Ile Val Leu Leu Ala Ala Leu Ala Leu Leu Phe
1               5                   10                  15

-continued

```
Gly Leu Gly Leu Ala Leu Thr Cys Ser Ser Asn Thr Ala Lys Ala Ala
             20                  25                  30
Thr
```